(12) United States Patent
Church et al.

(10) Patent No.: US 11,208,652 B2
(45) Date of Patent: Dec. 28, 2021

(54) MITOCHONDRIAL GENOME EDITING AND REGULATION

(71) Applicant: President and Fellows of Harvard College, Cambridge, MA (US)

(72) Inventors: George M. Church, Brookline, MA (US); Luhan Yang, Somerville, MA (US); Margo R. Monroe, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 136 days.

(21) Appl. No.: 16/075,247

(22) PCT Filed: Feb. 2, 2017

(86) PCT No.: PCT/US2017/016168
§ 371 (c)(1),
(2) Date: Aug. 3, 2018

(87) PCT Pub. No.: WO2017/136520
PCT Pub. Date: Aug. 10, 2017

(65) Prior Publication Data
US 2019/0062739 A1    Feb. 28, 2019

Related U.S. Application Data

(60) Provisional application No. 62/291,040, filed on Feb. 4, 2016.

(51) Int. Cl.
| | | |
|---|---|---|
| *C12N 15/113* | (2010.01) |
| *C12N 9/22* | (2006.01) |
| *C12N 15/10* | (2006.01) |
| *C12N 15/63* | (2006.01) |
| *C12N 7/00* | (2006.01) |
| *A61K 48/00* | (2006.01) |

(52) U.S. Cl.
CPC .............. *C12N 15/113* (2013.01); *C12N 7/00* (2013.01); *C12N 9/22* (2013.01); *C12N 15/102* (2013.01); *C12N 15/63* (2013.01); *A61K 48/00* (2013.01); *C12N 2310/20* (2017.05); *C12N 2750/14143* (2013.01); *C12N 2800/80* (2013.01)

(58) Field of Classification Search
CPC .................................................. C12N 15/113
See application file for complete search history.

(56) References Cited

U.S. PATENT DOCUMENTS

| | | | | |
|---|---|---|---|---|
| 2010/0111911 A1* | 5/2010 | Guy | ................... | A61K 48/0058 424/93.21 |
| 2016/0340661 A1* | 11/2016 | Cong | .................... | A61K 48/00 |
| 2019/0382794 A1* | 12/2019 | Patzel | ....................... | A61P 7/06 |

FOREIGN PATENT DOCUMENTS

| | | | | |
|---|---|---|---|---|
| WO | WO2015089462 | * | 6/2015 | ....... A01K 2227/105 |
| WO | 2015/134812 A1 | | 9/2015 | |
| WO | 2015/139139 A1 | | 9/2015 | |

OTHER PUBLICATIONS

Jo et al. ("Efficient Mitochondrial Genome Editing by CRISPR/Cas9." BioMed Research International. vol. 2015, Article ID 305716, 10 pages, http://dx.doi.org/10.1155/2015/305716) (Year: 2015).*
Yu et al. (PNAS. May 15, 2012 [published online Apr. 20, 2012]; 109(20): E1238-E1247). (Year: 2012).*
Jo, A et al. "Efficient Mitochondrial Genome Editing by CRISPR/Cas9. BioMed Research International." 2015, vol. 205, pp. 1-10; abstract; p. 2, second column, second-third paragraphs; p. 4, second paragraph; DOI: 10.1155/2015/305716.

* cited by examiner

*Primary Examiner* — Scott Long
(74) *Attorney, Agent, or Firm* — Banner & Witcoff, Ltd.

(57) ABSTRACT

Methods and compositions of altering mitochondrial DNA of a eukaryotic cell are provided using one or more of a mitochondrial specific adeno-associated virus to deliver one or more nucleic acids encoding CRISPR system including a Cas9 protein or its nuclease inactive variant and a guide RNA into a mitochondria for expression within the mitochondria. The Cas9 system can cut, nick or regulate a target mitochondrial nucleic acid.

7 Claims, 7 Drawing Sheets

Specification includes a Sequence Listing.

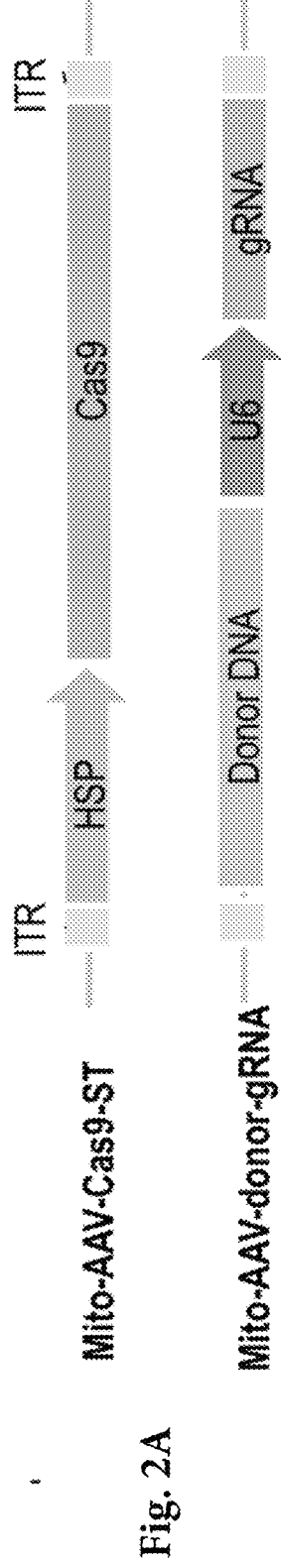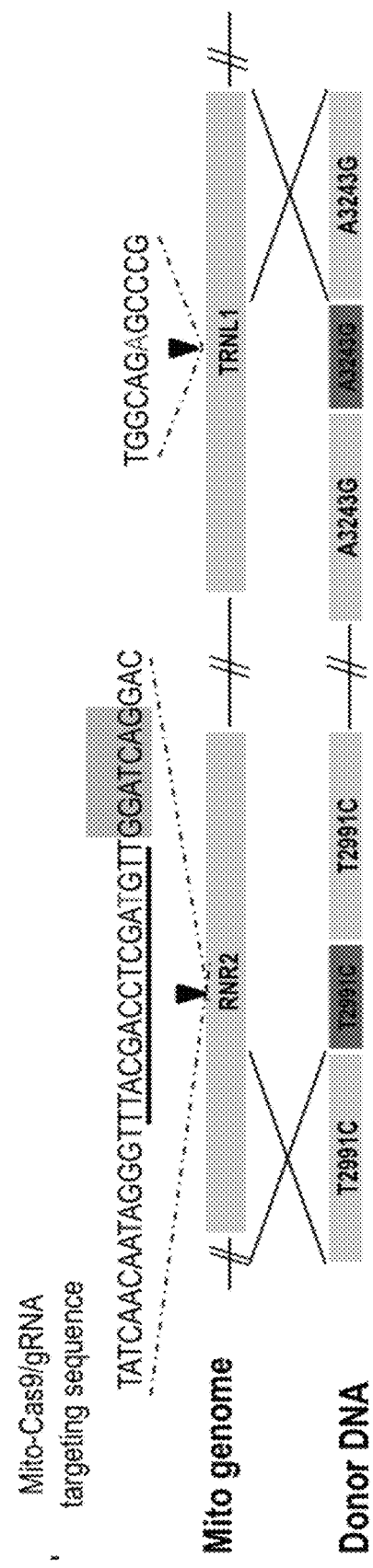
Fig. 2A
Fig. 2B

SEQUENCE LISTING

<160> NUMBER OF SEQ ID NOS: 13

<210> SEQ ID NO 1
<211> LENGTH: 54
<212> TYPE: DNA
<213> ORGANISM: Artificial
<220> FEATURE:
<223> OTHER INFORMATION: synthetic primer

<400> SEQUENCE: 1
acactctttc cctacacgac gctcttccga tcgcgctctc aacctaattt atga    54

<210> SEQ ID NO 2
<211> LENGTH: 54

```
<212> TYPE: DNA
<213> ORGANISM: Artificial
<220> FEATURE:
<223> OTHER INFORMATION: synthetic primer

<400> SEQUENCE: 2
gtgactggag ttcagacgtg tgctcttccg atctttgaac ctctgggaac aagg        54

<210> SEQ ID NO 3
<211> LENGTH: 51
<212> TYPE: DNA
<213> ORGANISM: Artificial
<220> FEATURE:
<223> OTHER INFORMATION: synthetic primer

<400> SEQUENCE: 3
acactctttc cctacacgac gctcttccga tcacttcaca aagcgccttc c           51

<210> SEQ ID NO 4
<211> LENGTH: 58
<212> TYPE: DNA
<213> ORGANISM: Artificial
<220> FEATURE:
<223> OTHER INFORMATION: synthetic primer

<400> SEQUENCE: 4
gtgactggag ttcagacgtg tgctcttccg atctgaagag gaattgaacc tctgactg    58

<210> SEQ ID NO 5
<211> LENGTH: 45
<212> TYPE: DNA
<213> ORGANISM: Artificial
<220> FEATURE:
<223> OTHER INFORMATION: synthetic primer

<400> SEQUENCE: 5
ccctacacga cgctcttccg atccaataac ttgaccaacg aaca                   45

<210> SEQ ID NO 6
<211> LENGTH: 45
<212> TYPE: DNA
<213> ORGANISM: Artificial
<220> FEATURE:
<223> OTHER INFORMATION: synthetic primer

<400> SEQUENCE: 6
gttcagacgt gtgctcttcc gatctacctt taatagcggc tgcac                  45

<210> SEQ ID NO 7
<211> LENGTH: 1386
<212> TYPE: DNA
<213> ORGANISM: Artificial
<220> FEATURE:
<223> OTHER INFORMATION: synthetic polynucleotide

<400> SEQUENCE: 7
cccaccccca attttgtatt tatttatttt ttaattattt tgtgcagcga tgggggcggg   60 ggggggggggg gggcgcgcgc caggcggggc ggggcggggc gagggcgggg gcggggcgag  120
gcggagaggt gcggcggcag ccaatcagag cggcgcgctc cgaaagtttc cttttatggc  180
gaggcggcgg cggcggcggc cctataaaaa gcgaagcgcg cggcgggcgg gagtcgctgc  240
gacgctgcct tcgccccgtg ccccgctccg ccgccgcctc gcgccgcccg cccggctct   300 gactgaccgc gttactccca caggtgagcg ggcgggacgg cccttctcct ccgggctgta  360
```

| | |
|---|---|
| attagcgctt ggtttaatga cggcttgttt cttttctgtg gctgcgtgaa agccttgagg | 420 |
| ggctccggga gggccctttg tgcgggggga gcggctcggg gctgtccgcg ggggacggc | 480 |
| tgccttcggg ggggacgggg cagggcgggg ttcggcttct ggcgtgtgac cggcggctct | 540 |
| agagcctctg ctaaccatgt tcatgccttc ttcttttttcc tacagctcct gggcaacgtg | 600 |
| ctggttattg tgctgtctca tcattttggc aaagaattgg atcgggatcc ccgggtaccg | 660 |
| gtcgccacca tggtgagcaa gggcgaggag ctgttcaccg gggtggtgcc catcctggtc | 720 |
| gagctggacg gcgacgtaaa cggccacaag ttcagcgtgt ccggcgaggg cgagggcgat | 780 |
| gccacctacg gcaagctgac cctgaagttc atctgcacca ccggcaagct gcccgtgccc | 840 |
| tggcccaccc tcgtgaccac cctgacctac ggcgtgcagt gcttcagccg ctaccccgac | 900 |
| cacatgaagc agcacgactt cttcaagtcc gccatgcccg aaggctacgt ccaggagcgc | 960 |
| accatcttct tcaaggacga cggcaactac aagacccgcg ccgaggtgaa gttcgagggc | 1020 |
| gacaccctgg tgaaccgcat cgagctgaag ggcatcgact tcaaggagga cggcaacatc | 1080 |
| ctggggcaca agctggagta caactacaac agccacaacg tctatatcat ggccgacaag | 1140 |
| cagaagaacg gcatcaaggt gaacttcaag atccgccaca acatcgagga cggcagcgtg | 1200 |
| cagctcgccg accactacca gcagaacacc cccatcggcg acggccccgt gctgctgccc | 1260 |
| gacaaccact acctgagcac ccagtccgcc ctgagcaaag accccaacga gaagcgcgat | 1320 |
| cacatggtcc tgctggagtt cgtgaccgcc gccgggatca ctctcggcat ggacgagctg | 1380 |
| tacaag | 1386 |

<210> SEQ ID NO 8
<211> LENGTH: 3422
<212> TYPE: DNA
<213> ORGANISM: Artificial
<220> FEATURE:
<223> OTHER INFORMATION: synthetic polynucleotide

<400> SEQUENCE: 8

| | |
|---|---|
| ccgctgctaa ccccataccc cgaaccaacc aaaccccaaa gacaccccc gccaccatga | 60 |
| gcgacctggt gctgggcctg acatcggca tcggcagcgt gggcgtgggc atcctgaaca | 120 |
| aggtgaccgg cgagatcatc cacaagaaca gtcgcatctt ccctgctgct caggctgaga | 180 |
| acaacctggt gcgccgcacc aaccgccagg tcgccggctc tgctcgccgc aagaagcacc | 240 |
| ggcgcgtgcg cctgaaccgc ctgttcgagg agagcggcct gatcaccgac ttcaccaaga | 300 |
| tcagcatcaa cctgaacccc taccagctgc gcgtgaaggg cctgaccgac gagctgagca | 360 |
| acgaggagct gttcatcgcc ctgaagaaca tggtgaagca ccgcggcatc agctacctgg | 420 |
| acgacgccag cgacgacggc aacagcagcg tgggcgacta cgcccagatc gtgaaggaga | 480 |
| acagcaagca gctggagacc aagaccccg gccagatcca gctggagcgc taccagaccct | 540 |
| acggccagct cgcggcgac ttcaccgtgg agaaggacgg caagaagcac cgcctgatca | 600 |
| acgtgttccc caccagcgcc taccgcagcg aggccctgcg catcctgcag acccagcagg | 660 |
| agttcaaccc ccagatcacc gacgagttca tcaaccgcta cctggagatc ctgaccggca | 720 |
| agcgcaagta ctaccacggc cccggcaacg agaagagccg caccgactac ggccgctacc | 780 |
| gcaccagcgg cgagaccctg acaacatct tcggcatcct gatcggcaag tgcaccttct | 840 |
| accccgacga gttccgcgcc gccaaggcca gctacaccgc ccaggagttc aacctgctga | 900 |
| acgacctgaa caacctgacc gtgccccaccg agaccaagaa gctgagcaag gagcagaaga | 960 |
| accagatcat caactacgtg aagaacgaga aggccatggg ccccgccaag ctgttcaagt | 1020 |

```
acatcgccaa gctgctgagc tgcgacgtgg ccgacatcaa gggctaccgc atcgacaaga      1080
gcggcaaggc cgagatccac accttcgagg cctaccgcaa gatgaagacc ctggagaccc      1140
tggacatcga gcagatggac cgcgagaccc tggacaagct ggcctacgtg ctgaccctga      1200
acaccgagcg cgagggcatc caggaggccc tggagcacga gttcgccgac ggcagcttca      1260
gccagaagca ggtggacgag ctggtgcagt ccgcaaggc caacagcagc atcttcggca      1320
agggctggca caacttcagc gtgaagctga tgatggagct gatccccgag ctgtacgaga      1380
ccagcgagga gcagatgacc atcctgaccc gcctgggcaa gcagaagacc accagcagca      1440
gcaacaagac caagtacatc gacgagaagc tgctgaccga ggagatctac aaccccgtgg      1500
tggccaagag cgtgcgccag gccatcaaga tcgtgaacgc cgccatcaag gagtacggcg      1560
acttcgacaa catcgtgatc gagatggccc gcgagaccaa cgaggacgac gagaagaagg      1620
ccatccagaa gatccagaag gccaacaagg acgagaagga cgccgccatg ctgaaggccg      1680
ccaaccagta caacggcaag gccgagctgc cccacagcgt gttccacggc cacaagcagc      1740
tggccaccaa gatccgcctg tggcaccagc agggcgagcg ctgcctgtac accggcaaga      1800
ccatcagcat ccacgacctg atcaacaaca gcaaccagtt cgaggtggac cacatcctgc      1860
ccctgagcat caccttcgac gacagcctgg ccaacaaggt gctggtgtac gccaccgcca      1920
accaggagaa gggccagcgc acccctaccc aggccctgga cagcatggac gacgcctgga      1980
gcttccgcga gctgaaggcc ttcgtgcgcg agagcaagac cctgagcaac aagaagaagg      2040
agtacctgct gaccgaggag gacatcagca agttcgacgt gcgcaagaag ttcatcgagc      2100
gcaacctggt ggacacccgc tacgccagcc gcgtggtgct gaacgccctg caggagcact      2160
tccgcgccca agatcgac accaaggtga gcgtggtgcg cggccagttc accagccagc      2220
tgcgccgcca ctggggcatc gagaagaccc gcgacaccta ccaccaccac gccgtggacg      2280
ccctgatcat tgcggcttct agccagctga acctgtggaa gaagcagaag aacacccctgg     2340 tgagctacag cgaggaccag ctgctggaca tcgagaccgg cgagctgatc agcgacgacg      2400
agtacaagga gagcgtgttc aaggcccct accagcactt cgtggacacc ctgaagagca      2460
aggagttcga ggacagcatc ctgttcagct accaggtgga cagcaagttc aaccgcaaga      2520
tcagcgacgc caccatctac gccacccgcc aggccaaggt gggcaaggac aaggccgacg      2580
agacctacgt gctgggcaag atcaaggaca tctacaccca ggacggctac gacgccttca      2640
tgaagatcta caagaaggac aagagcaagt tcctgatgta ccgccacgac ccccagacct      2700
tcgagaaggt gatcgagccc atcctggaga actaccccaa caagcagatc aacgataaag      2760
gcaaggaggt gcctgcaac cccttcctga gtacaagga ggagcacggc tacatccgca        2820
agtacagcaa gaaggcaac ggccccgaga tcaagagcct gaagtactac gacagcaagc      2880
tgggcaacca catcgacatc accccaagg acagcaacaa caggtggtg ctgcagagcg        2940 tgagcccctg cgcgccgac gtgtacttca caagaccac cggcaagtac gagatcctgg       3000
gcctgaagta cgccgacctg cagtttgata agggcaccgg cacctacaag atcagccagg      3060
agaagtacaa cgacatcaag aagaaggagg cgtggacag cgacagcgag ttcaagttca       3120
ccctgtacaa gaacgacctt ctgctggtga aggacacccga gaccaaggag caacagctgt     3180
tccgcttcct gagccgcacc atgcccaagc agaagcacta cgtggagctg aagccctacg      3240
acaagcagaa gttcgagggc ggcgaggccc tgatcaaggt gctgggcaac gtggccaaca      3300
gcggccagtg caagaagggc ctgggcaaga gcaacatcag catctacaag gtgcgcaccg      3360
```

| | |
|---|---|
| acgtgctggg caaccagcac atcatcaaga acgagggcga caagcccaag ctggacttct | 3420 |
| aa | 3422 |

<210> SEQ ID NO 9
<211> LENGTH: 6318
<212> TYPE: DNA
<213> ORGANISM: Artificial
<220> FEATURE:
<223> OTHER INFORMATION: synthetic polynucleotide
<220> FEATURE:
<221> NAME/KEY: misc_feature
<222> LOCATION: (1593)..(1593)
<223> OTHER INFORMATION: n is a, c, g, or t

<400> SEQUENCE: 9

| | |
|---|---|
| agcgcccaat acgcaaaccg cctctccccg cgcgttggcc gattcattaa tgcagctgcg | 60 |
| cgctcgctcg ctcactgagg ccgcccgggc aaagcccggg cgtcgggcga cctttggtcg | 120 |
| cccggcctca gtgagcgagc gagcgcgcag agagggagtg gccaactcca tcactagggg | 180 |
| ttccttgtag ttaatgatta acccgccatg ctacttatct acgtagccat gctctaggaa | 240 |
| gatcgtacca ttgacgtcaa taatgacgta tgttcccata gtaacgccaa tagggacttt | 300 |
| ccattgacgt caatgggtgg actatttacg gtaaactgcc cacttggcag tacatcaagt | 360 |
| gtatcatatg ccaagtacgc cccctattga cgtcaatgac ggtaaatggc ccgcctggca | 420 |
| ttatgcccag tacatgacct tatgggactt tcctacttgg cagtacatct acgtattagt | 480 |
| catcgctatt accatggtta gctggttgtc caagatagaa tcttagttca actttaaatt | 540 |
| tgcccacaga accctctaaa tccccttgta aatttaactg ttagtccaaa gaggaacagc | 600 |
| tctttggaca ctaggaaaaa accttgtaga gagagtaaaa aatttaacac ccatagtagg | 660 |
| cctaaaagca gccaccaatt aagaaagcgt tcaagctcaa cacccactac ctaaaaaatc | 720 |
| ccaaacatat aactgaactc ctcacaccca attggaccaa tctatcaccc tatagaagaa | 780 |
| ctaatgttag tataagtaac atgaaaacat tctcctccgc ataagcctgc gtcagattaa | 840 |
| aacactgaac tgacaattaa cagcccaata tctacaatca accaacaagt cattattacc | 900 |
| ctcactgtca acccaacaca ggcatgctca taaggaaagg ttaaaaaaag taaaggaac | 960 |
| tcggcaaatc ttaccccgcc tgtttaccaa aaacatcacc tctagcatca ccagtattag | 1020 |
| aggcaccgcc tgcccagtga cacatgttta acggccgcgg taccctaacc gtgcaaaggt | 1080 |
| agcataatca cttgttcctt aaatagggac ctgtatgaat ggctccacga gggttcagct | 1140 |
| gtctcttact tttaaccagt gaaattgacc tgcccgtgaa gaggcgggca taacacagca | 1200 |
| agacgagaag accctatgga gctttaattt attaatgcaa acagtaccta acaaacccac | 1260 |
| aggtcctaaa ctaccaaacc tgcattaaaa atttcggttg gggcgacctc ggagcagaac | 1320 |
| ccaacctccg agcagtacat gctaagactt caccagtcaa agcgaactac tatactcaat | 1380 |
| tgatccaata acttgaccaa cggaacaagt taccctaggg ataacagcgc aatcctattc | 1440 |
| tagagtccat atcaacaata gggtttacga cctcgacgtt ggatcaggac atcccgatgg | 1500 |
| tgcagccgct attaaaggtt cgtttgttca acgattaaag tcctacgtga tctgagttca | 1560 |
| gaccggagta atccaggtcg gtttctatct acnttcaaat tcctccctgt acgaaaggac | 1620 |
| aagagaaata aggcctactt cacaaagcgc cttcccccgt aaatgatatc atctcaactt | 1680 |
| agtattatac ccacacccac ccaagaacag ggtttgttaa gatggcaggg cccggtaatc | 1740 |
| gcataaaaact taaaacttta cagtcagagg ttcaattcct cttcttaaca acatacccat | 1800 |
| ggccaacctc ctactcctca ttgtacccat tctaatcgca atggcattcc taatgcttac | 1860 |

```
cgaacgaaaa attctaggct atatacaact acgcaaaggc cccaacgttg taggccccta    1920
cgggctacta caaccettcg ctgacgccat aaaactcttc accaaagagc ccctaaaacc    1980
cgccacatct accatcaccc tctacatcac cgccccgacc ttagctctca ccatcgctct    2040
tctactatga acccccctcc ccatacccaa cccctggtc aacctcaacc taggcctcct    2100
atttattcta gccacctcta gcctagccgt ttactcaatc ctctgatcag ggtgagcatc    2160
aaactcaaac tacgccctga tcggcgcact gcgagcagta gcccaaacaa tctcatatga    2220
agtcacccta gccatcattc tactatcaac attactaata agtggctcct ttaacctctc    2280 caccettatc acaacacaag aacacctctg attactcctg ccatcatgac ccttggccat    2340
aatatgattt atctccacac tagcagagac caaccgaacc cccttcgacc ttgccgaagg    2400
ggagtccgaa ctagtctcag gcttcaacat cgaatacgcc gcaggcccct tcgccctatt    2460
cttcatagcc gaatacacaa acattattat aataaacacc ctcaccacta caatcttcct    2520
aggaacaaca attagcgctt ggtttaatga cggcttgttt cttttctgta caaaaaagca    2580
ggctttaaag gaaccaattc agtcgactgg atccggtacc aaggtcgggc aggaagaggg    2640
cctatttccc atgattcctt catatttgca tatacgatac aaggctgtta gagagataat    2700
tagaattaat ttgactgtaa acacaaagat attagtacaa aatacgtgac gtagaaagta    2760
ataatttctt gggtagtttg cagttttaaa attatgtttt aaaatggact atcatatgct    2820
taccgtaact tgaaagtatt tcgatttctt ggctttatat atcttgtgga aaggacgaaa    2880
caccggataa cagcgcaatc ctattgtttt tgtactctca gaaatgcaga agctacaaag    2940
ataaggcttc atgccgaaat caacaccctg tcatttatg gcagggtgtt ttttgacct     3000 tgccgaaggg gagtccgaac tagtctcaga tgtacaaaaa agcaggcttt aaaggaacca    3060
attcagtcga ctggatccgg taccaaggtc gggcaggaag agggcctatt tccatgatt    3120 cettcatatt tgcatatacg atacaaggct gttagagaga taattagaat taatttgact    3180
gtaaacacaa agatattagt acaaaatacg tgacgtagaa agtaataatt tcttgggtag    3240
tttgcagttt taaaattatg ttttaaaatg gactatcata tgcttaccgt aacttgaaag    3300
tatttcgatt tcttggcttt atatatcttg tggaaaggac gaaacaccgt ttacgacctc    3360
gatgttggag tttttgtact ctcagaaatg cagaagctac aaagataagg cttcatgccg    3420
aaatcaacac cctgtcattt tatggcaggg tgttttttta agttaacaac aacaattgca    3480
ttcattttat gtttcaggtt caggggggaga tgtgggaggt tttttaaagc aagtaaaacc    3540
tctacaaatg tggtaaaatc gataaggatc ttcctagagc atggctacgt agataagtag    3600
catggcgggt taatcattaa ctacaaggaa cccctagtga tggagttggc cactccctct    3660
ctgcgcgctc gctcgctcac tgaggccggg cgaccaaagg tcgcccgacg cccgggcttt    3720
gcccgggcgg cctcagtgag cgagcgagcg cgcagcctta attaacctaa ttcactggcc    3780
gtcgttttac aacgtcgtga ctgggaaaac cctggcgtta cccaacttaa tcgccttgca    3840
gcacatcccc ctttcgccag ctggcgtaat agcgaagagg cccgcaccga tcgcccttcc    3900
caacagttgc gcagcctgaa tggcgaatgg gacgcgccct gtagcggcgc attaagcgcg    3960
gcgggtgtgg tggttacgcg cagcgtgacc gctacacttg ccagcgccct agcgcccgct    4020
cctttcgctt tcttccctttc ctttctcgcc acgttcgccg gctttccccg tcaagctcta    4080
aatcgggggc tccctttagg gttccgattt agtgctttac ggcacctcga ccccaaaaaa    4140
cttgattagg gtgatggttc acgtagtggg ccatcgccct gatagacggt ttttcgccct    4200
```

```
ttgacgttgg agtccacgtt ctttaatagt ggactcttgt tccaaactgg aacaacactc    4260
aaccctatct cggtctattc ttttgattta taagggattt tgccgatttc ggcctattgg    4320
ttaaaaaatg agctgattta acaaaaattt aacgcgaatt ttaacaaaat attaacgctt    4380
acaatttagg tggcactttt cggggaaatg tgcgcggaac ccctatttgt ttatttttct    4440
aaatacattc aaatatgtat ccgctcatga caataaacc ctgataaatg cttcaataat    4500
attgaaaaag gaagagtatg agtattcaac atttccgtgt cgcccttatt ccctttttg    4560 cggcattttg ccttcctgtt tttgctcacc cagaaacgct ggtgaaagta aaagatgctg    4620
aagatcagtt gggtgcacga gtgggttaca tcgaactgga tctcaacagc ggtaagatcc    4680
ttgagagttt tcgccccgaa gaacgttttc caatgatgag cacttttaaa gttctgctat    4740
gtggcgcggt attatcccgt attgacgccg ggcaagagca actcggtcgc cgcatacact    4800
attctcagaa tgacttggtt gagtactcac cagtcacaga aaagcatctt acggatggca    4860
tgacagtaag agaattatgc agtgctgcca taaccatgag tgataacact gcggccaact    4920
tacttctgac aacgatcgga ggaccgaagg agctaaccgc ttttttgcac aacatggggg    4980
atcatgtaac tcgccttgat cgttgggaac cggagctgaa tgaagccata ccaaacgacg    5040
agcgtgacac cacgatgcct gtagcaatgg caacaacgtt gcgcaaacta ttaactggcg    5100
aactacttac tctagcttcc cggcaacaat taatagactg gatggaggcg gataaagttg    5160
caggaccact tctgcgctcg gcccttccgg ctggctggtt tattgctgat aaatctggag    5220
ccggtgagcg tgggtctcgc ggtatcattg cagcactggg gccagatggt aagccctccc    5280
gtatcgtagt tatctacacg acggggagtc aggcaactat ggatgaacga atagacaga    5340 tcgctgagat aggtgcctca ctgattaagc attggtaact gtcagaccaa gtttactcat    5400
atatacttta gattgattta aaacttcatt tttaatttaa aaggatctag gtgaagatcc    5460
tttttgataa tctcatgacc aaaatccctt aacgtgagtt ttcgttccac tgagcgtcag    5520
accccgtaga aaagatcaaa ggatcttctt gagatccttt ttttctgcgc gtaatctgct    5580
gcttgcaaac aaaaaaacca ccgctaccag cggtggtttg tttgccggat caagagctac    5640
caactctttt tccgaaggta actggcttca gcagagcgca gataccaaat actgttcttc    5700
tagtgtagcc gtagttaggc caccacttca agaactctgt agcaccgcct acatacctcg    5760
ctctgctaat cctgttacca gtggctgctg ccagtggcga taagtcgtgt cttaccgggt    5820
tggactcaag acgatagtta ccggataagg cgcagcggtc gggctgaacg ggggggttcgt    5880 gcacacagcc cagcttggag cgaacgacct acaccgaact gagataccta cagcgtgagc    5940
tatgagaaag cgccacgctt cccgaaggga gaaaggcgga caggtatccg gtaagcggca    6000
gggtcggaac aggagagcgc acgagggagc ttccaggggg aaacgcctgg tatctttata    6060
gtcctgtcgg gtttcgccac ctctgacttg agcgtcgatt tttgtgatgc tcgtcagggg    6120
ggcggagcct atgaaaaaac gccagcaacg cggccttttt acggttcctg gccttttgct    6180
ggccttttgc tcacatgttc tttcctgcgt tatcccctga ttctgtggat aaccgtatta    6240
ccgcctttga gtgagctgat accgctcgcc gcagccgaac gaccgagcgc agcgagtcag    6300
tgagcgagga agcggaag                                                  6318
```

<210> SEQ ID NO 10
<211> LENGTH: 41
<212> TYPE: DNA
<213> ORGANISM: Artificial
<220> FEATURE:
<223> OTHER INFORMATION: synthetic oligonucleotide

```
<400> SEQUENCE: 10
tatcaacaat agggtttacg acctcgatgt tggatcagga c                          41

<210> SEQ ID NO 11
<211> LENGTH: 12
<212> TYPE: DNA
<213> ORGANISM: Artificial
<220> FEATURE:
<223> OTHER INFORMATION: synthetic oligonucleotide

<400> SEQUENCE: 11
tggcagagcc cg                                                          12

<210> SEQ ID NO 12
<211> LENGTH: 41
<212> TYPE: DNA
<213> ORGANISM: Artificial
<220> FEATURE:
<223> OTHER INFORMATION: targeting sequence figure 2B

<400> SEQUENCE: 12
tatcaacaat agggtttacg acctcgatgt tbgatcadga c                          41

<210> SEQ ID NO 13
<211> LENGTH: 12
<212> TYPE: DNA
<213> ORGANISM: Artificial
<220> FEATURE:
<223> OTHER INFORMATION: targeting sequence figure 2B

<400> SEQUENCE: 13
tggcagagcc cg                                                          12
```

MITOCHONDRIAL GENOME EDITING AND REGULATION

RELATED APPLICATION DATA

This application is a continuation of PCT application no. PCT/US2017/16168, designating the United States and filed Feb. 2, 2017, which claims the benefit of U.S. Provisional Application No. 62/291,040 filed on Feb. 4, 2016, which are hereby incorporated herein by reference in their entirety for all purposes.

STATEMENT OF GOVERNMENT INTERESTS

This invention was made with government support under Grant No. P50 HG005550 from the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 28, 2020, is named 010498.01120_WO_SL.txt and is 17,208 bytes in size.

BACKGROUND

Mitochondria dysfunction causes various fatal age-related and degenerative disorders. Many of these diseases arise from genetic mutations within the mitochondrial DNA (mtDNA) while others are caused by mutations within the nuclear genome (nDNA) responsible for mitochondrial maintenance. Despite advancements in understanding mitochondrial function, the breadth of pathogenic mtDNA mutations causative of various fatal clinical phenotypes challenge the ability to screen for potential therapeutics. For instance, mitochondrial encephalomyopathy, lactic acidosis, and stroke-like episodes (MELAS) is a heteroplasmic and maternal inheritance mitochondrial disorder that impairs the brain, nervous, and muscle systems. More than 80% of MELAS cases are caused by the A3243G mutation in the tRNA$^{Leu}$ gene, which regulates protein fabrication, oxygen consumption, and energy production. Although mutations responsible for MELAS are known, the lack of knowledge in pathophysiology remains unknown due to the inability to alter patient cell lines and/or generate MELAS mitochondrial disease models. Development of mitochondrial disease models could potentially facilitate drug discovery and disease understanding.

Bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli*. *Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus*. *Journal of Bacteriology* 190, 1390 (February, 2008).

SUMMARY

Aspects of the present disclosure are directed to a method of altering mitochondrial DNA using a Cas9 protein and a guide RNA which form a complex with a target mitochondrial nucleic acid sequence. According to one aspect, one or more mitochondria specific vectors, i.e. a vector capable of delivering a nucleic acid sequence into a mitochondria, include a CRISPR system, i.e. one or more nucleic acids encoding for a guide RNA and a Cas9 protein and/or alternatively a donor nucleic acid sequence, are used to deliver the CRISPR system to a target mitochondrial DNA sequence. According to this aspect, the CRISPR system is used to cut or nick the target mitochondrial DNA sequence or otherwise deliver a transcriptional regulator, such as a transcriptional activator or transcriptional repressor, to the target mitochondrial nucleic acid sequence.

According to one aspect, one or more mitochondria specific adeno-associated viruses (mito-AAV) which include a CRISPR system as described herein are used to deliver the CRISPR system to a target mitochondrial DNA sequence. According to this aspect, the CRISPR system is used to cut or nick the target mitochondrial DNA sequence or otherwise deliver a transcriptional regulator, such as a transcriptional activator or transcriptional repressor, to the target mitochondrial nucleic acid sequence.

According to certain aspects, a method of modulating expression of a target mitochondrial nucleic acid sequence in a mitochondria of a eukaryotic cell is provided including introducing into the mitochondria a first foreign nucleic acid encoding one or more guide RNAs complementary to one or more target mitochondrial nucleic acids, introducing into the mitochondria a second foreign nucleic acid encoding a Cas9 protein, such as a Cas9 enzyme, a Cas9 nickase or a nuclease null Cas9, introducing into the cell a third foreign nucleic acid encoding a transcriptional regulator protein or domain, wherein the one or more guide RNAs, the Cas9 protein, and the transcriptional regulator protein or domain are expressed, wherein the one or more guide RNAs, the Cas9 protein and the transcriptional regulator protein or domain co-localize to the target mitochondrial nucleic acid sequence and wherein the transcriptional regulator protein or domain regulates expression of the target mitochondrial nucleic acid.

According to one aspect, the foreign nucleic acid encoding the Cas9 protein further encodes the transcriptional regulator protein or domain to create an expression product or fusion of the Cas9 attached to the transcriptional regulator protein or domain. According to one aspect, the foreign nucleic acid encoding one or more guide RNAs further encodes a target of an RNA-binding domain and the foreign nucleic acid encoding the transcriptional regulator protein or domain further encodes an RNA-binding domain fused to the transcriptional regulator protein or domain.

According to one aspect, the transcriptional regulator protein or domain is a transcriptional activator. According to one aspect, the transcriptional regulator protein or domain upregulates expression of the target mitochondrial nucleic acid. According to one aspect, the transcriptional regulator protein or domain upregulates expression of the target mitochondrial nucleic acid to treat a disease or detrimental condition. According to one aspect, the target mitochondrial nucleic acid is associated with a disease or detrimental condition. According to one aspect, the transcriptional regulator protein or domain is a transcriptional repressor. According to one aspect, the transcriptional regulator protein or domain downregulates expression of the target mitochondrial nucleic acid. According to one aspect, the transcriptional regulator protein or domain downregulates expression of the target mitochondrial nucleic acid to treat a disease or detrimental condition. According to one aspect, the target nucleic acid is associated with a disease or detrimental condition.

According to one aspect of altering a target mitochondrial nucleic acid, two or more guide RNAs may be used with a Cas9 nickase wherein the Cas9 nickase co-localizes with the two or more guide RNAs to the target mitochondrial nucleic acid and nicks the target mitochondrial nucleic acid resulting in two or more adjacent nicks. According to one aspect, the two or more adjacent nicks are on the same strand of the double stranded target mitochondrial nucleic acid. According to one aspect, the two or more adjacent nicks are on the same strand of the double stranded target mitochondrial nucleic acid and result in homologous recombination. According to one aspect, the two or more adjacent nicks are on different strands of the double stranded target mitochondrial nucleic acid. According to one aspect, the two or more adjacent nicks are on different strands of the double stranded target mitochondrial nucleic acid and create double stranded breaks. According to one aspect, the two or more adjacent nicks are on different strands of the double stranded target mitochondrial nucleic acid and create double stranded breaks resulting in nonhomologous end joining. According to one aspect, the two or more adjacent nicks are on different strands of the double stranded target mitochondrial nucleic acid and are offset with respect to one another. According to one aspect, the two or more adjacent nicks are on different strands of the double stranded target mitochondrial nucleic acid and are offset with respect to one another and create double stranded breaks. According to one aspect, the two or more adjacent nicks are on different strands of the double stranded target mitochondrial nucleic acid and are offset with respect to one another and create double stranded breaks resulting in nonhomologous end joining.

According to one aspect, the two or more adjacent nicks are on different strands of the double stranded DNA and create double stranded breaks resulting in fragmentation of the target nucleic acid thereby preventing expression of the target nucleic acid.

According to one aspect, the method further includes introducing into the cell a third foreign nucleic acid encoding a donor nucleic acid sequence wherein the two or more nicks results in incorporation of the donor nucleic acid sequence into the target mitochondrial nucleic acid through homologous recombination or nonhomologous end joining.

According to one aspect, a construct is provided that includes a mito-AAV and a nucleic acid encoding a Cas9 protein. According to another aspect, a construct is provided that includes a mito-AAV and a nucleic acid encoding a gRNA. According to one aspect, a construct is provided that includes a mito-AAV, a donor nucleic acid sequence and a nucleic acid sequence encoding a gRNA.

According to one aspect, a eukaryotic cell is provided wherein mitochondria therein include a nucleic acid encoding a guide RNA sequence complementary to a target mitochondrial nucleic acid sequence, a nucleic acid encoding a Cas9 enzyme that interacts with the guide RNA sequence and cleaves the target mitochondrial nucleic acid sequence in a site specific manner, wherein the mitochondria expresses the guide RNA and the Cas9 enzyme, the guide RNA binds to the complementary target nucleic acid and the Cas9 enzyme cleaves the target mitochondrial nucleic acid in a site specific manner.

According to another aspect, a eukaryotic cell is provided wherein mitochondria therein include a guide RNA sequence complementary to a target mitochondrial nucleic acid sequence, a donor nucleic acid sequence, and a Cas9 enzyme that interacts with the guide RNA sequence and cleaves the target mitochondrial nucleic acid sequence in a site specific manner, wherein the guide RNA sequence binds to the complementary target mitochondrial nucleic acid sequence and the Cas9 enzyme cleaves the target mitochondrial nucleic acid sequence in a site specific manner; and wherein the donor sequence is integrated into the mitochondrial nucleic acid sequence.

According to one aspect, a eukaryotic cell is provided wherein mitochondria therein include a guide RNA complementary to the target mitochondrial nucleic acid sequence, a Cas9 protein having inactive nuclease domains, wherein the Cas9 protein having inactive nuclease domains includes a transcriptional activator or repressor domain connected thereto for modulating target mitochondrial nucleic acid expression in vivo, wherein the guide RNA and the Cas9 protein including the transcriptional activator or repressor domain co-localize at the target mitochondrial nucleic acid sequence and wherein the transcriptional activator or repressor domain modulates expression of the target mitochondrial nucleic acid sequence.

According to one aspect, a eukaryotic cell is provided wherein mitochondria therein include a guide RNA complementary to the target mitochondrial nucleic acid sequence, with the guide RNA having a transcriptional activator or repressor domain connected thereto for modulating target mitochondrial nucleic acid expression in vivo, a Cas9 protein having inactive nuclease domains, wherein the guide RNA and the Cas9 protein co-localize at the target mitochondrial nucleic acid sequence and wherein the transcriptional activator or repressor domain modulates expression of the target mitochondrial nucleic acid sequence.

According to another aspect, a eukaryotic cell is provided wherein mitochondria therein include a guide RNA complementary to the target mitochondrial nucleic acid sequence, a Cas9 protein having inactive nuclease domains, a transcriptional activator or repressor domain for modulating target mitochondrial nucleic acid expression in vivo, wherein the transcriptional activator or repressor domain becomes attached to either the guide RNA or the Cas9 protein, wherein the guide RNA and the Cas9 protein co-localize at the target mitochondrial nucleic acid sequence and wherein the transcriptional activator or repressor domain modulates expression of the target mitochondrial nucleic acid sequence.

Further features and advantages of certain embodiments of the present invention will become more fully apparent in the following description of embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which:

FIG. 1A is a schematic of rAAV-GFP. FIG. 1B depicts in schematic the minimal CAG promoter (CAG), the minor or distal heavy-strand promoter (HSP) responsible for mRNA transcription in mitochondria; ATG start codon and ATA mitochondria specific start codon and AGA stop codon and AGG mitochondria specific stop codon. The AGA stop codon and AGG mitochondria specific stop codon were tested to confirm mitochondrial targeting. As shown in the images, mitochondria specific start codon or/and stop codon constrains the expression of rAAV-GFP specifically in the mitochondria, as evidenced in the colocalization of GFP and mito-tracker signal.

FIG. 2A to FIG. 2D are directed to genotype and phenotype data confirming mitochondrial genome engineering. FIG. 2A is a schematic design of targeting the 16sRNA of mitochondria genome using mito-AAV-CRISPR system. FIG. 2B is a schematic showing co-transduction of mito-AAV-Cas9 with mito-AAV-donor-gRNA virus editing the mtDNA to confer CAP resistance in HT1080 and CAP resistance and MELAS variant in PGP1 iPS cells. Co-transduction of the two components generates a cut (dark triangle). The targeting sequence (underline), PAM sequence of Cas9-ST, intended T2991C mutation (red) on RNR2 (16sRNA) and A3243G mutation (ref) on TRNL1 coding sequence are illustrated. The sequences of Donor DNA and gRNA are provided. Figure discloses SEQ ID NOS 10-11, respectively, in order of appearance. FIG. 2C depicts data demonstrating that HT1080 mitochondria are engineered with 0.6% homologous recombination (HR) efficiency and iPS cells are engineered with 0.3% HR efficiency. No difference between non-homologous end-joining (NHEJ) repair between positive and negative controls is measured. FIG. 2D depicts data demonstrating that engineered mitochondria are significantly more viable to concentrations of CAP after 7 days, (t-test, * p<0.001  p<0.05 N=3.) (SEQ ID NOs: 12-13).

FIG. 3A is an image of mouse retina imaged using fluorescence microscopy. Green dots indicate transduced retinal cells expressing GFP. The mouse was sacrificed at 50 days after subretinal injections of AAV-CAG-GFP. FIG. 3B depicts data derived from GFP+ cells being enriched and sequenced to quantify HR efficiency as measured by deep sequencing. The average HR efficiency of each group is shown and error bars represent standard error from the mean.

DETAILED DESCRIPTION

Figure 1A:
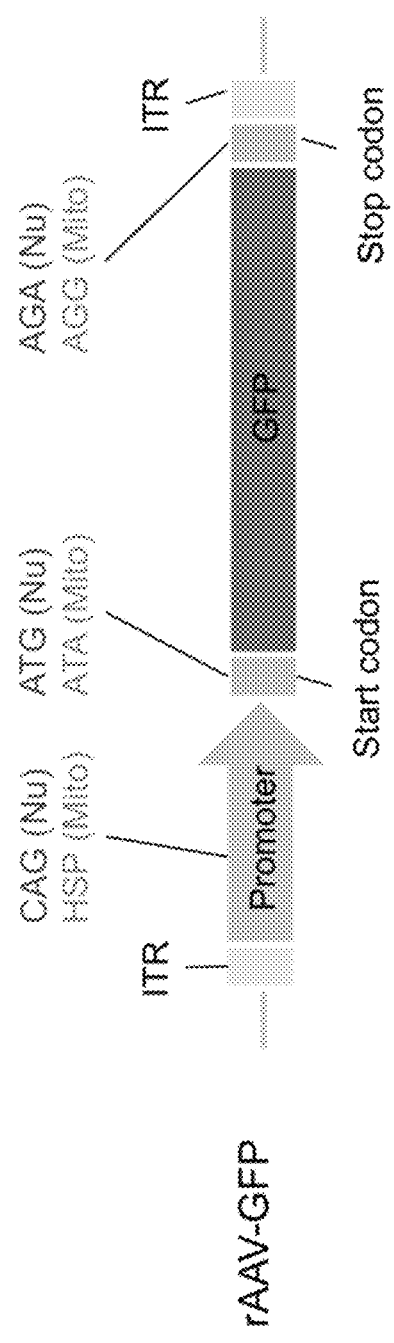
FIG. 1A to FIG. 1B are directed to targeting mitochondria DNA using an engineered mito-AAV.

Embodiments of the present disclosure are directed to methods of targeting mitochondrial nucleic acid for editing or transcriptional regulation. According to one aspect, one or more vectors are used to introduce one or more nucleic acids encoding a CRISPR system, i.e. a Cas9 protein and a guide RNA, and optionally a donor nucleic acid sequence, into mitochondria of a eukaryotic cell for editing or transcriptional regulation. The nucleic acids are expressed and the CRISPR system cuts or nicks the mitochondrial nucleic acid or otherwise delivers a transcriptional regulator to the mitochondrial nucleic acid. Together, a guide RNA and a Cas9 protein are referred to as a co-localization complex as that term is understood by one of skill in the art to the extent that the guide RNA and the Cas9 protein complex with a target mitochondrial nucleic acid. According to certain aspects, a vector may include one or more nucleic acids encoding a Cas9 protein, a guide RNA and/or a donor nucleic acid sequence. According to certain aspects, one or more nucleic acids encoding a Cas9 protein, a guide RNA and/or a donor nucleic acid sequence may be present within the same vector or present within different vectors.

According to one aspect, a vector is engineered to specifically target the mitochondria and deliver the one or more nucleic acids encoding a Cas9 protein, a guide RNA and/or a donor nucleic acid sequence into the mitochondria for expression by the mitochondrial DNA. According to one aspect, an exemplary vector includes a promoter responsible for mRNA transcription in mitochondria, a mitochondria specific start codon and a mitochondria specific stop codon. According to this aspect, expression of the one or more nucleic acids encoding a Cas9 protein, a guide RNA and/or a donor nucleic acid sequence is limited to expression within the mitochondria. According to one aspect, an exemplary vector is a mitochondria-specific adeno-associated virus, such as those known in the art. According to one aspect, a mitochondria-specific adeno-associated virus includes a nucleic acid encoding a Cas9 protein and promoters and codons to express the nucleic acid encoding a Cas9 protein within the mitochondria. According to one aspect, a mitochondria-specific adeno-associated virus includes a nucleic acid encoding a guide RNA and promoters and codons to express the nucleic acid encoding the guide RNA within the mitochondria. According to one aspect, a mitochondria-specific adeno-associated virus includes a donor nucleic acid sequence or a nucleic acid encoding a donor nucleic acid sequence to provide the donor nucleic acid sequence within the mitochondria or otherwise Cas9 protein and promoters and codons to express the nucleic acid encoding the donor nucleic acid sequence under operation of a suitable promoter and start and stop codons within the mitochondria. According to one aspect, a mitochondria-specific adeno-associated virus includes a nucleic acid encoding a Cas9 protein, a nucleic acid encoding a guide RNA and a nucleic acid encoding the donor nucleic sequence and a suitable promoter(s) and start and stop codon(s). According to one aspect, a mitochondria-specific adeno-associated virus includes a nucleic acid encoding a guide RNA and a nucleic acid encoding the donor nucleic sequence and a suitable promoter(s) and start and stop codon(s).

Cas9 Description

RNA guided DNA binding proteins are readily known to those of skill in the art to bind to DNA for various purposes. Such DNA binding proteins may be naturally occurring. DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., *Nature Reviews*,

*Microbiology*, Vol. 9, June 2011, pp. 467-477 including all supplementary information hereby incorporated by reference in its entirety.

In general, bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli. Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus. Journal of Bacteriology* 190, 1390 (February, 2008).

Three classes of CRISPR systems are generally known and are referred to as Type I, Type II or Type III). According to one aspect, a particular useful enzyme according to the present disclosure to cleave dsDNA is the single effector enzyme, Cas9, common to Type II. See K. S. Makarova et al., Evolution and classification of the CRISPR-Cas systems. *Nature reviews. Microbiology* 9, 467 (Jim, 2011) hereby incorporated by reference in its entirety. Within bacteria, the Type II effector system consists of a long pre-crRNA transcribed from the spacer-containing CRISPR locus, the multifunctional Cas9 protein, and a tracrRNA important for gRNA processing. The tracrRNAs hybridize to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9. TracrRNA-crRNA fusions are contemplated for use in the present methods.

According to one aspect, the enzyme of the present disclosure, such as Cas9 unwinds the DNA duplex and searches for sequences matching the crRNA to cleave. Target recognition occurs upon detection of complementarity between a "protospacer" sequence in the target DNA and the remaining spacer sequence in the crRNA. Importantly, Cas9 cuts the DNA only if a correct protospacer-adjacent motif (PAM) is also present at the 3' end. According to certain aspects, different protospacer-adjacent motif can be utilized. For example, the *S. pyogenes* system requires an NGG sequence, where N can be any nucleotide. *S. thermophilus* Type II systems require NGGNG (see P. Horvath, R. Barrangou, CRISPR/Cas, the immune system of bacteria and archaea. *Science* 327, 167 (Jan. 8, 2010) hereby incorporated by reference in its entirety and NNAGAAW (see H. Deveau et al., Phage response to CRISPR-encoded resistance in *Streptococcus thermophilus. Journal of bacteriology* 190, 1390 (February, 2008) hereby incorporatd by reference in its entirety), respectively, while different *S. mutans* systems tolerate NGG or NAAR (see J. R. van der Ploeg, Analysis of CRISPR in *Streptococcus mutans* suggests frequent occurrence of acquired immunity against infection by M102-like bacteriophages. *Microbiology* 155, 1966 (June, 2009) hereby incorporated by reference in its entirety. Bioinformatic analyses have generated extensive databases of CRISPR loci in a variety of bacteria that may serve to identify additional useful PAMs and expand the set of CRISPR-targetable sequences (see M. Rho, Y. W. Wu, H. Tang, T. G. Doak, Y. Ye, Diverse CRISPRs evolving in human microbiomes. *PLoS genetics* 8, e1002441 (2012) and D. T. Pride et al., Analysis of streptococcal CRISPRs from human saliva reveals substantial sequence diversity within and between subjects over time. *Genome research* 21, 126 (January, 2011) each of which are hereby incorporated by reference in their entireties.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinek et al., *Science* 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: *Methanococcus maripaludis* C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua; Lactobacillus casei; Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans; Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium* botulinum B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum; Mycoplasma mobile* 163K; *Mycoplasma penetrans; Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni doylei* 269 97; *Campylobacter jejuni* 81116; *Campylobacter jejuni; Campylobacter lari* RM2100; *Helicobacter hepaticus; Wolinella succinogenes; Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida; Francisella tularensis novicida* U112; *Francisella tularensis holarctica; Francisella tularensis* FSC 198; *Francisella tularensis tularensis; Francisella tularensis* WY96-3418; and *Treponema denticola* ATCC 35405. The Cas9 protein may be referred by one of skill in the art in the literature as Csn1. An exemplary *S. pyogenes* Cas9 protein sequence is provided in Deltcheva et al., *Nature* 471, 602-607 (2011) hereby incorporated by reference in its entirety.

Modification to the Cas9 protein is a representative embodiment of the present disclosure. CRISPR systems useful in the present disclosure are described in R. Barrangou, P. Horvath, CRISPR: new horizons in phage resistance and strain identification. *Annual review of food science and technology* 3, 143 (2012) and B. Wiedenheft, S. H. Sternberg, J. A. Doudna, RNA-guided genetic silencing systems in bacteria and archaea. *Nature* 482, 331 (Feb. 16, 2012) each of which are hereby incorporated by reference in their entireties.

According to certain aspects, the DNA binding protein is altered or otherwise modified to inactivate the nuclease activity. Such alteration or modification includes altering one or more amino acids to inactivate the nuclease activity or the nuclease domain. Such modification includes removing the polypeptide sequence or polypeptide sequences exhibiting nuclease activity, i.e. the nuclease domain, such that the polypeptide sequence or polypeptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein includes polypeptide sequences modified to inactivate nuclease activity or removal of a polypeptide sequence or sequences to inactivate nuclease activity. The nuclease-null DNA binding protein retains the ability to bind to DNA even though the nuclease activity has been inactivated. Accordingly, the DNA binding protein includes the polypeptide sequence or sequences required for DNA binding but may lack the one or more or all of the nuclease sequences exhibiting nuclease activity. Accordingly, the DNA binding protein includes the polypeptide sequence or sequences required for DNA binding but may have one or more or all of the nuclease sequences exhibiting nuclease activity inactivated.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase. An exemplary DNA binding protein is an RNA guided DNA binding protein nuclease of a Type II CRISPR System, such as a Cas9 protein or modified Cas9 or homolog of Cas9. An exemplary DNA binding protein is a Cas9 protein nickase. An exemplary DNA binding protein is an RNA guided DNA binding protein of a Type II CRISPR System which lacks nuclease activity. An exemplary DNA binding protein is a nuclease-null or nuclease deficient Cas9 protein.

According to an additional aspect, nuclease-null Cas9 proteins are provided where one or more amino acids in Cas9 are altered or otherwise removed to provide nuclease-null Cas9 proteins. According to one aspect, the amino acids include D10 and H840. See Jinek et al., *Science* 337, 816-821 (2012). According to an additional aspect, the amino acids include D839 and N863. According to one aspect, one or more or all of D10, H840, D839 and H863 are substituted with an amino acid which reduces, substantially eliminates or eliminates nuclease activity. According to one aspect, one or more or all of D10, H840, D839 and H863 are substituted with alanine. According to one aspect, a Cas9 protein having one or more or all of D10, H840, D839 and H863 substituted with an amino acid which reduces, substantially eliminates or eliminates nuclease activity, such as alanine, is referred to as a nuclease-null Cas9 ("Cas9Nuc") and exhibits reduced or eliminated nuclease activity, or nuclease activity is absent or substantially absent within levels of detection. According to this aspect, nuclease activity for a Cas9Nuc may be undetectable using known assays, i.e. below the level of detection of known assays.

According to one aspect, the Cas9 protein, Cas9 protein nickase or nuclease null Cas9 includes homologs and orthologs thereof which retain the ability of the protein to bind to the DNA and be guided by the RNA. According to one aspect, the Cas9 protein includes the sequence as set forth for naturally occurring Cas9 from *S. thermophiles* or *S. pyogenes* and protein sequences having at least 30%, 40%, 50%, 60%, 70%, 80%, 90%, 95%, 98% or 99% homology thereto and being a DNA binding protein, such as an RNA guided DNA binding protein.

An exemplary CRISPR system includes the *S. thermophiles* Cas9 nuclease (ST1 Cas9) (see Esvelt K M, et al., Orthogonal Cas9 proteins for RNA-guided gene regulation and editing, Nature Methods., (2013) hereby incorporated by reference in its entirety). An exemplary CRISPR system includes the *S. pyogenes* Cas9 nuclease (Sp. Cas9), an extremely high-affinity (see Sternberg, S. H., Redding, S., Jinek, M., Greene, E. C. & Doudna, J. A. DNA interrogation by the CRISPR RNA-guided endonuclease Cas9. *Nature* 507, 62-67 (2014) hereby incorporated by reference in its entirety), programmable DNA-binding protein isolated from a type II CRISPR-associated system (see Garneau, J. E. et al. The CRISPR/Cas bacterial immune system cleaves bacteriophage and plasmid DNA. *Nature* 468, 67-71 (2010) and Jinek, M. et al. A programmable dual-RNA-guided DNA endonuclease in adaptive bacterial immunity. *Science* 337, 816-821 (2012) each of which are hereby incorporated by reference in its entirety). According to certain aspects, a nuclease null or nuclease deficient Cas 9 can be used in the methods described herein. Such nuclease null or nuclease deficient Cas9 proteins are described in Gilbert, L. A. et al.

CRISPR-mediated modular RNA-guided regulation of transcription in eukaryotes. *Cell* 154, 442-451 (2013); Mali, P. et al. CAS9 transcriptional activators for target specificity screening and paired nickases for cooperative genome engineering. *Nature biotechnology* 31, 833-838 (2013); Maeder, M. L. et al. CRISPR RNA-guided activation of endogenous human genes. *Nature methods* 10, 977-979 (2013); and Perez-Pinera, P. et al. RNA-guided gene activation by CRISPR-Cas9-based transcription factors. *Nature methods* 10, 973-976 (2013) each of which are hereby incorporated by reference in its entirety. The DNA locus targeted by Cas9 (and by its nuclease-deficient mutant, "dCas9" precedes a three nucleotide (nt) 5'-NGG-3' "PAM" sequence, and matches a 15-22-nt guide or spacer sequence within a Cas9-bound RNA cofactor, referred to herein and in the art as a guide RNA. Altering this guide RNA is sufficient to target Cas9 or a nuclease deficient Cas9 to a target nucleic acid. In a multitude of CRISPR-based biotechnology applications (see Mali, P., Esvelt, K. M. & Church, G. M. Cas9 as a versatile tool for engineering biology. *Nature methods* 10, 957-963 (2013); Hsu, P. D., Lander, E. S. & Zhang, F. Development and Applications of CRISPR-Cas9 for Genome Engineering. *Cell* 157, 1262-1278 (2014); Chen, B. et al. Dynamic imaging of genomic loci in living human cells by an optimized CRISPR/Cas system. *Cell* 155, 1479-1491 (2013); Shalem, O. et al. Genome-scale CRISPR-Cas9 knockout screening in human cells. *Science* 343, 84-87 (2014); Wang, T., Wei, J. J., Sabatini, D. M. & Lander, E. S. Genetic screens in human cells using the CRISPR-Cas9 system. *Science* 343, 80-84 (2014); Nissim, L., Perli, S. D., Fridkin, A., Perez-Pinera, P. & Lu, T. K. Multiplexed and Programmable Regulation of Gene Networks with an Integrated RNA and CRISPR/Cas Toolkit in Human Cells. *Molecular cell* 54, 698-710 (2014); Ryan, O. W. et al. Selection of chromosomal DNA libraries using a multiplex CRISPR system. *eLife* 3 (2014); Gilbert, L. A. et al. Genome-Scale CRISPR-Mediated Control of Gene Repression and Activation. *Cell* (2014); and Citorik, R. J., Mimee, M. & Lu, T. K. Sequence-specific antimicrobials using efficiently delivered RNA-guided nucleases. *Nature biotechnology* (2014) each of which are hereby incorporated by reference in its entirety), the guide is often presented in a so-called sgRNA (single guide RNA), wherein the two natural Cas9 RNA cofactors (gRNA and tracrRNA) are fused via an ngineered loop or linker.

According to one aspect, the Cas9 protein is an enzymatically active Cas9 protein, a Cas9 protein wild-type protein, a Cas9 protein nickase or a nuclease null or nuclease deficient Cas9 protein. Additional exemplary Cas9 proteins include Cas9 proteins attached to, bound to or fused with functional proteins such as transcriptional regulators, such as transcriptional activators or repressors, a Fok-domain, such as Fok 1, an aptamer, a binding protein, PP7, MS2 and the like.

According to certain aspects, the Cas9 protein may be delivered directly to a cell by methods known to those of skill in the art, including injection or lipofection, or as translated from its cognate mRNA, or transcribed from its cognate DNA into mRNA (and thereafter translated into protein). Cas9 DNA and mRNA may be themselves introduced into cells through electroporation, transient and stable transfection (including lipofection) and viral transduction or other methods known to those of skill in the art.

Guide RNA Description

Embodiments of the present disclosure are directed to the use of a CRISPR/Cas system and, in particular, a guide RNA which may include one or more of a spacer sequence, a tracr mate sequence and a tracr sequence. The term spacer sequence is understood by those of skill in the art and may include any polynucleotide having sufficient complementarity with a target nucleic acid sequence to hybridize with the target nucleic acid sequence and direct sequence-specific binding of a CRISPR complex to the target sequence. The guide RNA may be formed from a spacer sequence covalently connected to a tracr mate sequence (which may be referred to as a crRNA) and a separate tracr sequence, wherein the tracr mate sequence is hybridized to a portion of the tracr sequence. According to certain aspects, the tracr mate sequence and the tracr sequence are connected or linked such as by covalent bonds by a linker sequence, which construct may be referred to as a fusion of the tracr mate sequence and the tracr sequence. The linker sequence referred to herein is a sequence of nucleotides, referred to herein as a nucleic acid sequence, which connect the tracr mate sequence and the tracr sequence. Accordingly, a guide RNA may be a two component species (i.e., separate crRNA and tracr RNA which hybridize together) or a unimolecular species (i.e., a crRNA-tracr RNA fusion, often termed an sgRNA).

According to certain aspects, the guide RNA is between about 10 to about 500 nucleotides. According to one aspect, the guide RNA is between about 20 to about 100 nucleotides. According to certain aspects, the spacer sequence is between about 10 and about 500 nucleotides in length. According to certain aspects, the tracr mate sequence is between about 10 and about 500 nucleotides in length. According to certain aspects, the tracr sequence is between about 10 and about 100 nucleotides in length. According to certain aspects, the linker nucleic acid sequence is between about 10 and about 100 nucleotides in length.

According to one aspect, embodiments described herein include guide RNA having a length including the sum of the lengths of a spacer sequence, tracr mate sequence, tracr sequence, and linker sequence (if present). Accordingly, such a guide RNA may be described by its total length which is a sum of its spacer sequence, tracr mate sequence, tracr sequence, and linker sequence (if present). According to this aspect, all of the ranges for the spacer sequence, tracr mate sequence, tracr sequence, and linker sequence (if present) are incorporated herein by reference and need not be repeated. A guide RNA as described herein may have a total length based on summing values provided by the ranges described herein. Aspects of the present disclosure are directed to methods of making such guide RNAs as described herein by expressing constructs encoding such guide RNA using promoters and terminators and optionally other genetic elements as described herein.

According to certain aspects, the guide RNA may be delivered directly to a cell as a native species by methods known to those of skill in the art, including injection or lipofection, or as transcribed from its cognate DNA, with the cognate DNA introduced into cells through electroporation, transient and stable transfection (including lipofection) and viral transduction.

Donor Description

The term "donor nucleic acid" include a nucleic acid sequence which is to be inserted into mitochondrial DNA according to methods described herein for expression by the mitochondrial DNA. The donor nucleic acid sequence may be expressed by the cell.

According to one aspect, the donor nucleic acid is exogenous to the cell. According to one aspect, the donor nucleic acid is foreign to the cell. According to one aspect, the donor nucleic acid is non-naturally occurring within the cell.

Transcription Regulator Description

According to one aspect, an engineered Cas9-gRNA system is provided which enables RNA-guided mitochondrial DNA regulation in human cells by tethering transcriptional activation domains to either a nuclease-null Cas9 or to guide RNAs. According to one aspect of the present disclosure, one or more transcriptional regulatory proteins or domains (such terms are used interchangeably) are joined or otherwise connected to a nuclease-deficient Cas9 or one or more guide RNA (gRNA). The transcriptional regulatory domains correspond to targeted loci. Accordingly, aspects of the present disclosure include methods and materials for localizing transcriptional regulatory domains to targeted loci by fusing, connecting or joining such domains to either Cas9N or to the gRNA.

According to one aspect, a Cas9N-fusion protein capable of transcriptional activation is provided. According to one aspect, a VP64 activation domain (see Zhang et al., *Nature Biotechnology* 29, 149-153 (2011) hereby incorporated by reference in its entirety) is joined, fused, connected or otherwise tethered to the C terminus of Cas9N. According to one method, the transcriptional regulatory domain is provided to the site of target mitochondrial DNA by the Cas9N protein. According to one method, a Cas9N fused to a transcriptional regulatory domain is provided within a cell along with one or more guide RNAs. The Cas9N with the transcriptional regulatory domain fused thereto bind at or near target mitochondrial DNA. The one or more guide RNAs bind at or near target mitochondrial DNA. The transcriptional regulatory domain regulates expression of the target mitochondrial nucleic acid sequence. According to a specific aspect, a Cas9N-VP64 fusion activated transcription of reporter constructs when combined with gRNAs targeting sequences near the promoter, thereby displaying RNA-guided transcriptional activation.

According to one aspect, a gRNA-fusion protein capable of transcriptional activation is provided. According to one aspect, a VP64 activation domain is joined, fused, connected or otherwise tethered to the gRNA. According to one method, the transcriptional regulatory domain is provided to the site of target mitochondrial DNA by the gRNA. According to one method, a gRNA fused to a transcriptional regulatory domain is provided within a cell along with a Cas9N protein. The Cas9N binds at or near target mitochondrial DNA. The one or more guide RNAs with the transcriptional regulatory protein or domain fused thereto bind at or near target mitochondrial DNA. The transcriptional regulatory domain regulates expression of the target gene. According to a specific aspect, a Cas9N protein and a gRNA fused with a transcriptional regulatory domain activated transcription of reporter constructs, thereby displaying RNA-guided transcriptional activation.

Transcriptional regulator proteins or domains which are transcriptional activators include VP16 and VP64 and others readily identifiable by those skilled in the art based on the present disclosure.

Target Mitochondrial Nucleic Acid

Target mitochondrial nucleic acids include any nucleic acid sequence within mitochondrial DNA to which a co-localization complex as described herein can be useful to either cut, nick or regulate. Target nucleic acids include mitochondrial nucleic acid sequences capable of being expressed into proteins. For purposes of the present disclosure, mitochondrial DNA, such as double stranded mitochondrial DNA, can include the target mitochondrial nucleic acid and a co-localization complex can bind to or otherwise co-localize with the mitochondrial DNA at or adjacent or near the target mitochondrial nucleic acid and in a manner in which the co-localization complex may have a desired effect on the target mitochondrial nucleic acid. One of skill based on the present disclosure will readily be able to identify or design guide RNAs and Cas9 proteins which co-localize to a mitochondrial DNA including a target mitochondrial nucleic acid. One of skill will further be able to identify transcriptional regulator proteins or domains which likewise co-localize to a mitochondrial DNA including a target mitochondrial nucleic acid.

Foreign Nucleic Acids Description

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

Cells

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, fungal cells, archael cells, eubacterial cells and the like. Cells include eukaryotic cells such as yeast cells, plant cells, and animal cells. Particular cells include mammalian cells. Further, cells include any in which it would be beneficial or desirable to cut, nick or regulate a target nucleic acid. Such cells may include those which are deficient in expression of a particular protein within the mitochondria leading to a disease or detrimental condition. Such diseases or detrimental conditions are readily known to those of skill in the art. According to the present disclosure, the nucleic acid responsible for expressing the particular protein may be targeted by the methods described herein and a transcriptional activator resulting in upregulation of the target nucleic acid and corresponding expression of the particular protein. In this manner, the methods described herein provide therapeutic treatment. Such cells may include those which are over express a particular protein in the mitochondria leading to a disease or detrimental condition. Such diseases or detrimental conditions are readily known to those of skill in the art. According to the present disclosure, the nucleic acid responsible for expressing the particular protein may be targeted by the methods described herein and a transcriptional depressor resulting in downregulation of the target nucleic acid and corresponding expression of the particular protein. In this manner, the methods described herein provide therapeutic treatment.

According to one aspect, the cell is a eukaryotic cell. According to one aspect, the cell is a yeast cell, a plant cell or an animal cell. According to one aspect, the cell is a mammalian cell. According to one aspect, the cell is a human cell. According to one aspect, the cell is a stem cell whether adult or embryonic. According to one aspect, the cell is a pluripotent stem cell. According to one aspect, the cell is an induced pluripotent stem cell. According to one aspect, the cell is a human induced pluripotent stem cell.

Vectors

Vectors are contemplated for use with the methods and constructs described herein. The term "vector" includes a nucleic acid molecule capable of transporting another nucleic acid to which it has been linked. Vectors used to deliver the nucleic acids to cells as described herein include vectors known to those of skill in the art and used for such purposes. Certain exemplary vectors may be plasmids, lentiviruses or adeno-associated viruses known to those of skill in the art. Vectors include, but are not limited to, nucleic acid molecules that are single-stranded, doublestranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, lentiviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Methods of non-viral delivery of nucleic acids or native DNA binding protein, native guide RNA or other native species include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term native includes the protein, enzyme or guide RNA species itself and not the nucleic acid encoding the species. According to certain aspects, the vectors are engineered to specifically target to mitochondria and/or codon optimized for mitochondrial specific delivery of the nucleic acid sequences within the vectors.

Regulatory Elements and Terminators and Tags

Regulatory elements are contemplated for use with the methods and constructs described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter and Pol II promoters described herein. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Aspects of the methods described herein may make use of terminator sequences. A terminator sequence includes a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. Terminator sequences include those known in the art and identified and described herein.

Aspects of the methods described herein may make use of epitope tags and reporter gene sequences. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, betaglucuronidase, luciferase, green fluorescent protein (GFP), HcRed, DsRed, cyan fluorescent protein (CFP), yellow fluorescent protein (YFP), and autofluorescent proteins including blue fluorescent protein (BFP).

Delivery Description

Embodiments of the present disclosure are directed to a method of delivering a Cas9 protein to cells within a subject comprising administering to the subject, such as systemically administering to the subject, such as by intravenous administration or injection, intraperitoneal administration or injection, intramuscular administration or injection, intracranial administration or injection, intraocular administration or injection, subcutaneous administration or injection, a Cas9 protein or a nucleic acid encoding the Cas9 protein.

Embodiments of the present disclosure are directed to a method of delivering a guide RNA having an RNA domain (selected RNA sequence) attached thereto to cells within a subject comprising administering to the subject, such as systemically administering to the subject, such as by intravenous administration or injection, intraperitoneal administration or injection, intramuscular administration or injection, intracranial administration or injection, intraocular administration or injection, subcutaneous administration or injection, a guide RNA or a nucleic acid encoding the guide RNA.

Embodiments of the present disclosure are directed to a method of delivering a Cas9 protein and a guide RNA to cells within a subject comprising administering to the subject, such as systemically administering to the subject, such as by intravenous administration or injection, intraperitoneal administration or injection, intramuscular administration or injection, intracranial administration or injection, intraocular administration or injection, subcutaneous administration or injection, a Cas9 protein or a nucleic acid encoding the Cas9 protein and a guide RNA or a nucleic acid encoding the guide RNA.

Diseases and Conditions Associated with Mitochondrial DNA

Mitochondrial mutations trigger various degenerative disorder, cancer, and aging. Mitochondria dysfunction causes various fatal age-related and degenerative disorders. See D. C. Wallace, Mitochondrial diseases in man and mouse. *Science* 283, 1482-1488 (1999); F. Terasaki, M. Tanaka, K. Kawamura, Y. Kanzaki, M. Okabe, T. Hayashi, H. Shimomura, T. Ito, M. Suwa, J. S. Gong, J. Zhang, Y. Kitaura, A case of cardiomyopathy showing progression from the hypertrophic to the dilated form: association of Mt8348A-->G mutation in the mitochondrial tRNA(Lys) gene with severe ultrastructural alterations of mitochondria in cardiomyocytes. *Jpn Circ J* 65, 691-694 (2001); G. M. Martin, L. A. Loeb, Ageing: mice and mitochondria. *Nature* 429, 357-359 (2004); S. G. Jarrett, A. S. Lewin, M. E. Boulton, The importance of mitochondria in age-related and inherited eye disorders. *Ophthalmic research* 44, 179-190 (2010); O. Z. Karicheva, O. A. Kolesnikova, T. Schirtz, M. Y. Vysokikh, A. M. Mager-Heckel, A. Lombes, A. Boucheham, I. A. Krasheninnikov, R. P. Martin, N. Entelis, I. Tarassov, Correction of the consequences of mitochondrial 3243A>G mutation in the MT-TL1 gene causing the MELAS syndrome by tRNA import into mitochondria. *Nucleic Acids Res* 39, 8173-8186 (2011); A. S. Tulah, M. A. Birch-Machin, Stressed out mitochondria: the role of mitochondria in ageing and cancer focussing on strategies and opportunities in human skin. *Mitochondrion* 13, 444-453 (2013); and W. J. Koopman, P. H. Willems, J. A. Smeitink, Monogenic mitochondrial disorders. *The New England journal of medicine* 366, 1132-1141 (2012). Many of these diseases arise from genetic mutations within the mitochondrial DNA (mtDNA) while others are caused by mutations within the nuclear genome (nDNA) responsible for mitochondrial maintenance.

For example, mitochondrial encephalomyopathy, lactic acidosis, and stroke-like episodes (MELAS) is a heteroplasmic and maternal inheritance mitochondrial disorder that impairs the brain, nervous, and muscle systems. More than 80% of MELAS cases are caused by the A3243G mutation in the tRNA$^{Leu}$ gene, which regulates protein fabrication, oxygen consumption, and energy production.

Diseases and detrimental conditions may be characterized by abnormal loss of expression or underexpression of a particular protein or abnormal gain or overexpression of a particular protein. Such diseases or detrimental conditions can be treated by upregulation or down regulation of the particular protein. Accordingly, methods of treating a disease or detrimental condition are provided where the co-localization complex as described herein associates or otherwise binds to mitochondrial DNA including a target mitochondrial nucleic acid, and the transcriptional activator of the co-localization complex upregulates expression of the target nucleic acid or the transcriptional repressor of the co-localization complex downregulates expression of the target nucleic acid. One of skill in the art will readily identify such diseases and detrimental conditions associated with mitochondrial DNA based on the present disclosure.

Mutations in mitochondrial DNA are known to result in alteration and pathological development in mitochondrial function and mitochondrial diseases, as well as cancer, diabetes, cardiovascular diseases, neurodegenerative disorders and aging (See, Alexeyev M. et al., The Maintenance of Mitochondrial DNA Integrity—Critical Analysis and Update, *Cold Spring Harb Perspect Biol*, (2013); 5:a012641). Accordingly, methods of treating a disease or detrimental condition are provided where foreign DNA is integrated into a mitochondrial nucleic acid sequence of a eukaryotic cell via providing to the mitochondria a guide RNA sequence complementary to a target mitochondrial nucleic acid sequence, providing to the mitochondria a donor sequence, providing to the mitochondrial a Cas9 enzyme that interacts with the guide RNA sequence and cleaves the target mitochondrial nucleic acid sequence in a site specific manner, wherein the guide RNA sequence binds to the complementary target mitochondrial nucleic acid sequence and the Cas9 enzyme cleaves the target mitochondrial nucleic acid sequence in a site specific manner; and wherein the donor sequence is integrated into the mitochondrial nucleic acid sequence.

The following examples are set forth as being representative of the present disclosure. These examples are not to be construed as limiting the scope of the present disclosure as these and other equivalent embodiments will be apparent in view of the present disclosure, figures and accompanying claims.

Example I

Materials and Methods

Cell Lines

HT 1080 cells were initially grown and maintained in Dulbecco's modified Eagle's medium (DMEM, Invitrogen) high glucose supplemented with 10% fetal bovine serum (Invitrogen), penicillin/streptomycin (pen/strep, Invitrogen) and nonessential amino acids (Invitrogen). After AAV transduction, the HT1080 cell lines were maintained in Dulbecco's modified eagle medium with no glucose supplemented with 10 mM galactose, 10% fetal bovine serum (Invitrogen), penicillin/streptomycin (pen/strep, Invitrogen), nonessential amino acids (Invitrogen), 5 mM sodium pyruvate (Invitrogen), and 5 mM HEPES (Invitrogen). The PGP1 iPS cells were grown and maintained in mTeSR1 basal medium (mTeSR1, Stemcell Technologies) with 1×mTeSR1 Supplement and penicillin/streptomycin (pen/strep, Invitrogen).

AAV-GFP Quality Control

AAV-CAG-GFP ($7.4 \times 10^{11}$ GC/mL) and mito-AAV-HSP-GFP ($3 \times 10^{11}$ GC/mL) were produced and were used to infect HT1080 seeded at 200,000 cells in a 12 well plate at $2.0 \times 10^{10}$ genome copies respectively. After 3 days post virus transduction, the number of infected HT1080 cells was visualized using optical fluorescence microscopy and quantified by flow cytometry.

Transfection

HT1080 Cells

A mito-AAV-Cas9 and mito-AAV-donor-RNR2$^{T2991C}$-gRNA were constructed and co-transduced to target and modify the RNR2 (16sRNA) gene with a T2991C mutation. HT1080 cells transduced with mito-AAV-Cas9 and HT1080 wild type served as negative controls. The infected cells were cultured for 7 days under normal conditions to allow the mito-AAVs to dilute out of the cells (Day 0). Next, the infected cells were harvested and plated at 15,000 cells per 9.5 cm$^2$ (1 well of a 6 well plate) and cultured in triplicates of 0, 150, 300 and 500 µg/mL CAP and harvested after 7 days.

Human PGP1 iPS Cells

A mito-AAV-Cas9 and mito-AAV-donor-RNR2$^{T2991C}$-TRNL1$^{A3243G}$-gRNA were co-transduced into PGP1 iPS cells to target and modify both the RNR2 (16sRNA) gene with a T2991C mutation and the TRNL1 (tRNA$^{Leu}$) gene with the A3243G mutation to create a selectable and programmable cell line to potentially model MELAS. Viable engineered HT1080 cells and HT1080 transduced with only mito-AAV-Cas9 ('Negative') cells were then seeded at 80,000 cells per 9.5 cm$^2$ and cultured in galactose (or glucose free) media spiked with 250 µg/mL CAP. See G. Manfredi, N. Gupta, M. E. Vazquez-Memije, J. E. Sadlock, A. Spinazzola, D. C. De Vivo, E. A. Schon, Oligomycin induces a decrease in the cellular content of a pathogenic mutation in the human mitochondrial ATPase 6 gene. *J Biol Chem* 274, 9386-9391 (1999); and B. H. Robinson, R. Petrova-Benedict, J. R. Buncic, D. C. Wallace, Nonviability of cells with oxidative defects in galactose medium: a screening test for affected patient fibroblasts. Biochemical medicine and metabolic biology 48, 122-126 (1992) each of which are hereby incorporated by reference in its entirety.

Co-Localization of Mitochondria and Mito-AAV-GFP

To confirm localization of mito-AAV-GFP into the mitochondria, after four days, the mitochondrion of the HT1080 cells transduced with mito-AAV-GFP were stained with nuclear and/or mitochondrial codons with MitoTracker® Deep Red FM according to manufacturer's protocol (Life Technologies). After 30 minutes incubation, the cells were rinsed with 1×PBS and the transduced and stained cells were imaged using confocal microscopy to check for co-localization.

Next-Generation Sequencing Analysis

Cell Harvest

Cells were rinsed with PBS, trypsinized, and harvested by centrifuging at 1000×g for 4 minutes.

Next-Generation Sequencing and Analysis

Genomic mtDNA was extracted using prepGEM (Zygem); targeted amplification of engineered mtDNA were amplified using specially designed illumine adaptor primers and prepared for NGS through PCR and analyzed according to L. Yang, M. Guell, S. Byrne, J. L. Yang, A. De Los Angeles, P. Mali, J. Aach, C. Kim-Kiselak, A. W. Briggs, X. Rios, P. Y. Huang, G. Daley, G. Church, Optimization of scarless human stem cell genome editing. *Nucleic Acids Res* 41, 9049-9061 (2013) hereby incorporated by reference in its entirety.

Cell Viability Assay

Figure 2C:
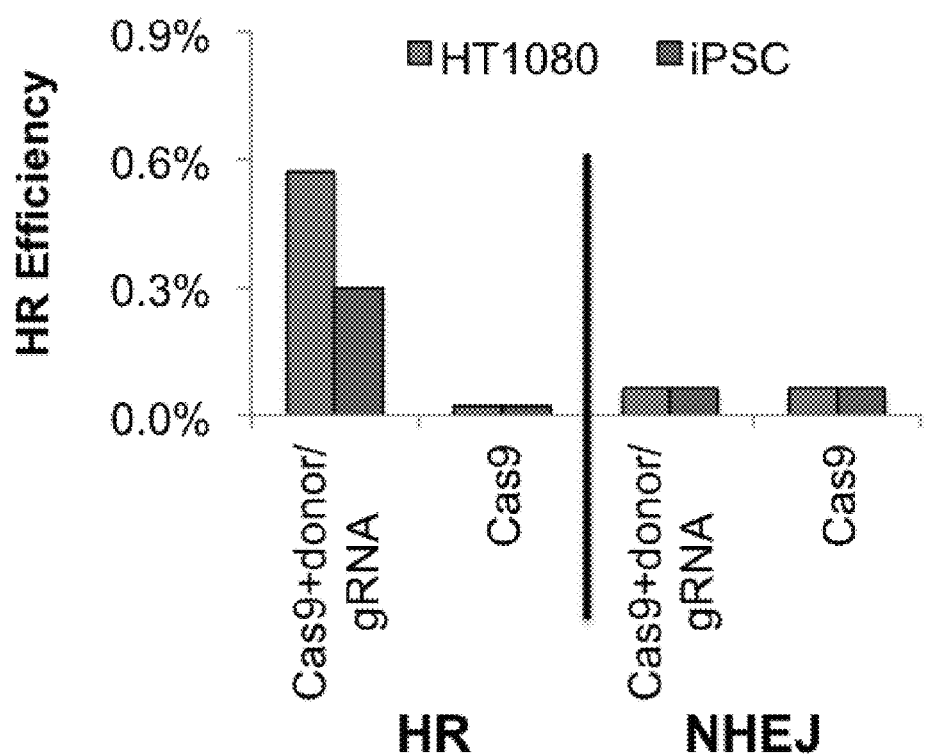

Transduced HT1080 cells that cultured in triplicates of 0, 150, 300 and 500 µg/mL CAP and harvested after 7 days (FIG. 2B) were harvested and checked for viability using trypan blue solution, 0.4% (Life Technologies).

In Vivo Retina Studies

Injections

Neonatal CD-1 mice (Charles River Laboratories) were used for all injections. All animal experiments in this study were approved by the Institutional Animal Care and Use Committee at Harvard University. Subretinal viral injections were performed on male and female pups using a Femtojet Express pressure injector (Eppendorf; 920010521) and glass micropipets (Origio; C060609). For experiments where GFP was analyzed using anti-GFP immunohistochemistry, ~0.1 µl of AAV ($7 \times 10^{11}$ GC/ml) was used, and for the FACS sorting ~0.1 µl of AAV ($2 \times 10^{13}$ GC/ml) was used. Animals were sacrificed at p20-p120. For the FACS sorting experiments, retinae were enzymatically dissociated with a papain mix, and gentle pipetting.

Immunohistochemistry

At p50, mouse eyeballs were fixed for 2 h in 4% PFA in PBS (pH 7.4). Retinae were then dissected out in PBS, and washed 3× in PBS for 10 minutes each. Whole retinae were blocked for 1 hour in 0.3% Triton, 0.02% SDS, 1% BSA in PBS. Samples were then incubated in primary antibody (Rabbit anti-GFP, Invitrogen, A6455, 1:500) overnight at 4° C. Next day, retinae were washed three times in 1×PBS and incubated for 3 h with donkey anti-rabbit Cy3 fluorescently coupled secondary antibody (1:250). Slides were washed three times with 1×PBS 15 min each, where the last wash contained DAPI (Invitrogen, D1306). Finally, retinae were mounted using Fluoromount-G (Southern Biotech, 0100-01)

Example II

Engineered mt-AAV

Figure 4:
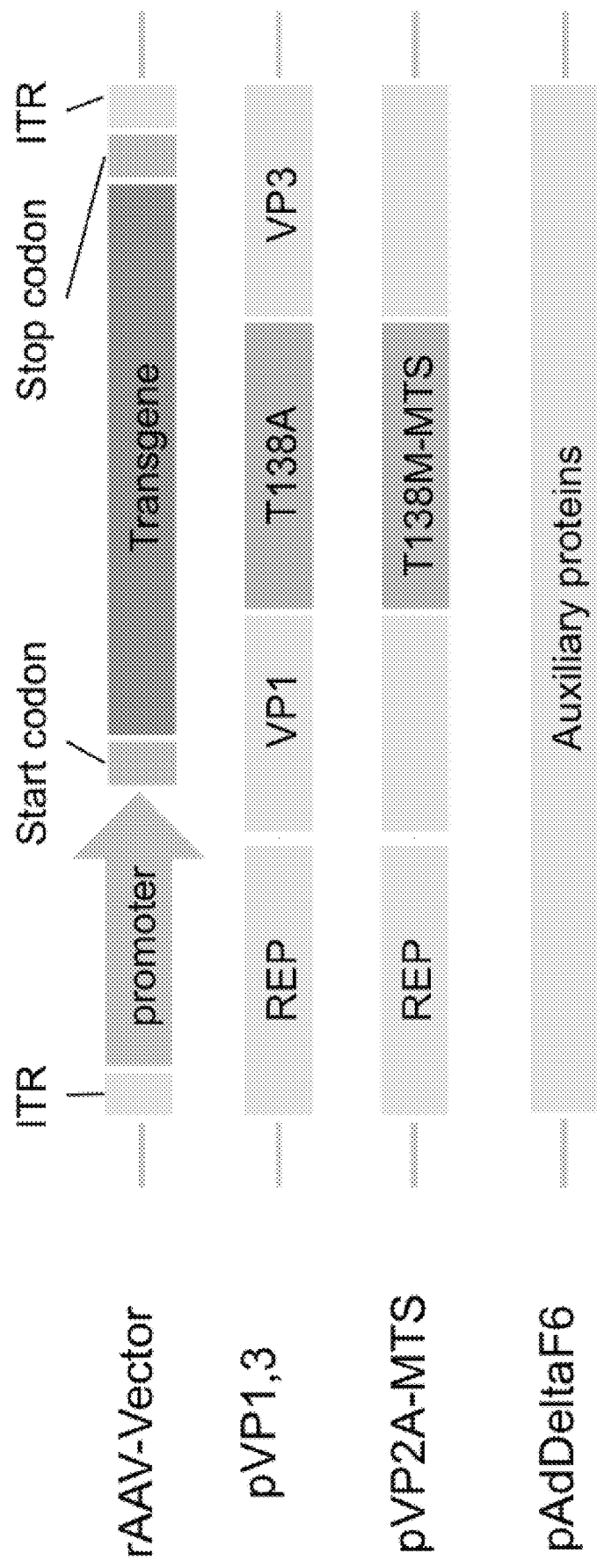
FIG. 4 is a schematic of mito-AAV generation.

Four constructs as shown in FIG. 4 were made as described above and were used to generate engineered mito-AAV: pVP1,3 and pVP2A-MTS encoding the capsid proteins, rAAV-vector with selected transgene, and pAdDeltaF6 containing auxiliary proteins. See H. Yu, R. D. Koilkonda, T. H. Chou, V. Porciatti, S. S. Ozdemir, V. Chiodo, S. L. Boye, S. E. Boye, W. W. Hauswirth, A. S. Lewin, J. Guy, Gene delivery to mitochondria by targeting modified adenoassociated virus suppresses Leber's hereditary optic neuropathy in a mouse model. *Proc Natl Acad Sci USA* 109, E1238-1247 (2012) hereby incorporated by reference in its entirety.

Figure 1B:
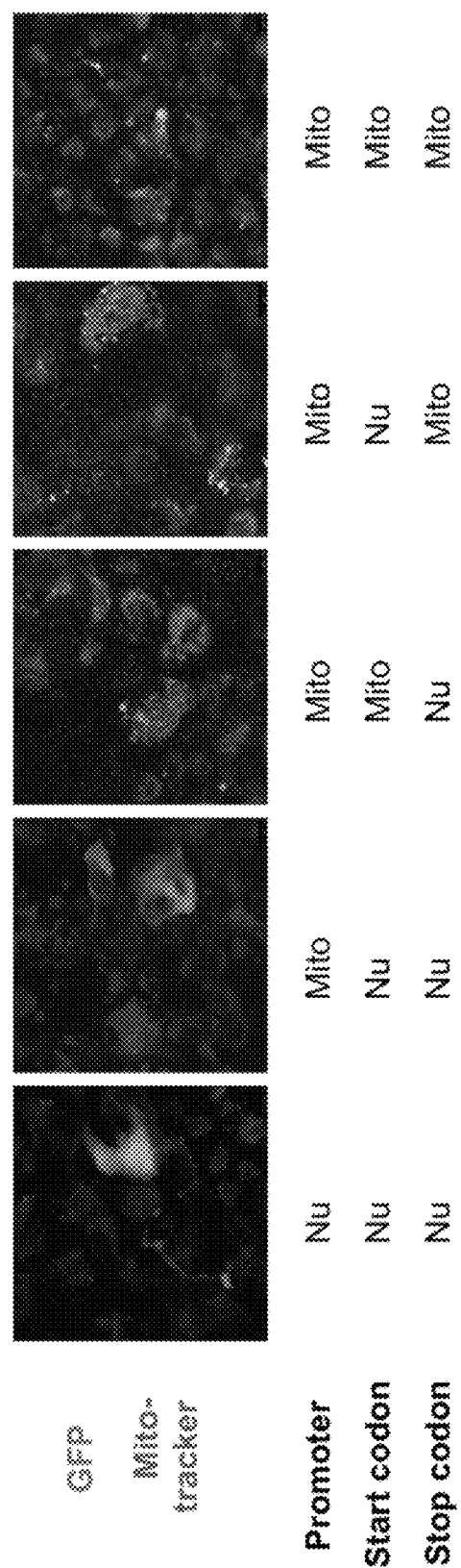
Figure 5A:
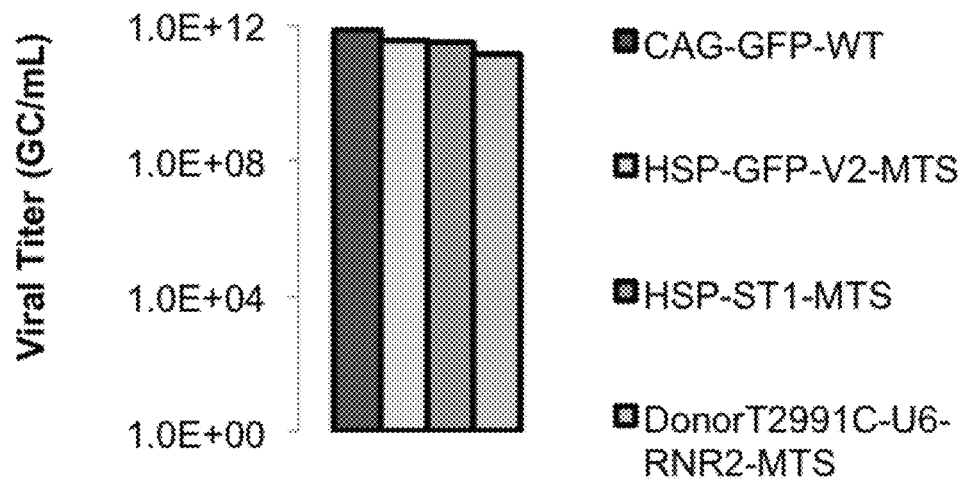
FIG. 5A depicts data directed to viral titer.
Figure 5B:
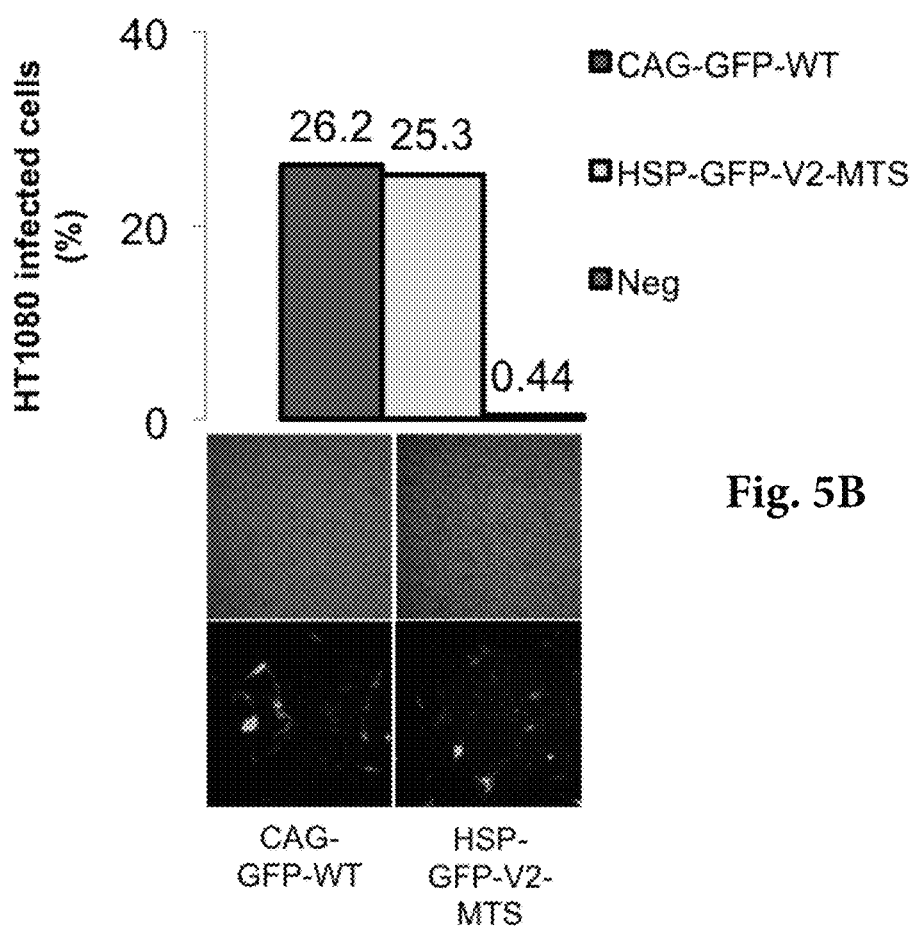
FIG. 5B depicts data directed to infected cells.

The viral capsid protein VP2 was first engineered by fusing it with a mitochondrial targeting sequence (MTS) of the COX8 (mito-AAV) according to *Proc Natl Acad Sci USA* 109, E1238-1247 (2012). To constrain the expression of the rAAV cargo in the mitochondria, five versions of rAAV-GFP were generated varying the promoters as well as the protein codon of GFP (See FIG. 1A): 1) minimal CAG promoter (CAG); 2) the minor or distal heavy-strand promoter (HSP) responsible for mRNA transcription in mitochondria; 3) HSP promoter with ATA mitochondria specific start codon; 4) HSP with AGA stop codon; and 5) HSP with AGG mitochondria specific stop codon. Notably, mitochondria specific start codon and/or stop codon constrain(s) the expression of rAAV-GFP specifically to the mitochondria, evidenced as the colocalization of GFP and mito-tracker signal. See FIG. 1B. See also FIGS. 5A and 5B which provide data relating to viral titer and infectionality of CAG-GFP, WT ("CAG-GFP-WT"); HSP-GFP, VP1,3, VP2-MTS ("HSP-GFP-V2-MTS"); HSP-Cas9-ST, VP1,3, VP2-MTS ("HSP-ST1-MTS"); and Donor-gRNA, VP2-MTS "(Donor-Mutation-U6-TargetGene-MTS") AVV vectors in HT1080 cells. FIG. 5A shows that titer yield, which was quantified by QuickTiter™ AAV Quantitation Kit (Cell Biolabs), was not affected by packaging contents. Each virus was transduced at 2×1010 genome copies into HT1080 cells. As shown in FIG. 5B, flow cytometry was used to quantify number of HT1080 cells infected to compare the infectionality of engineered viral particle V.S. wild type CAG-GFP-WT. Neg refers to wild-type HT1080 cells.

Figure 2D:
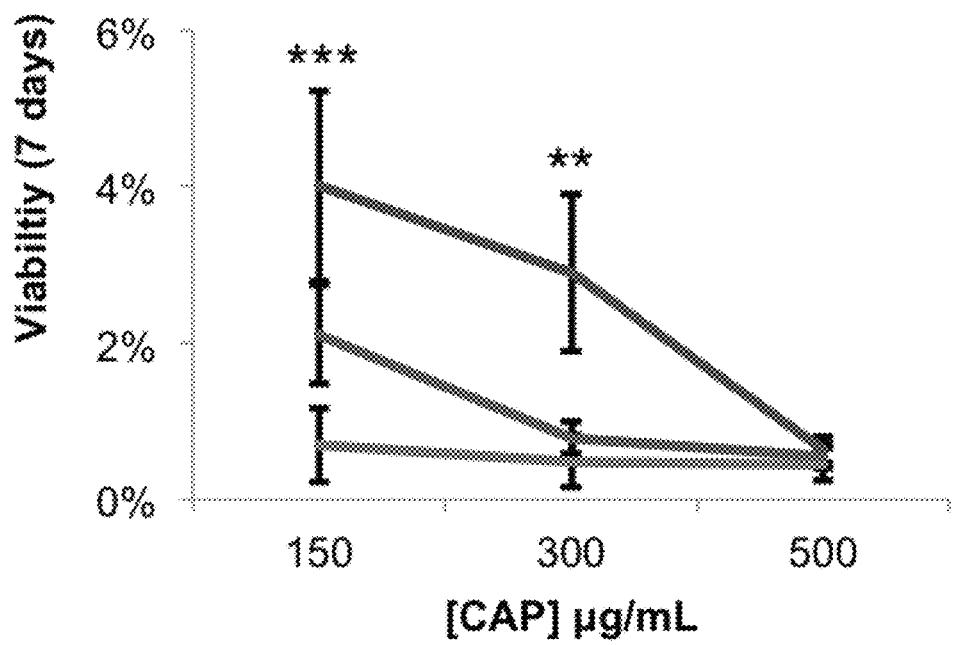
Figures 6A, 6B:
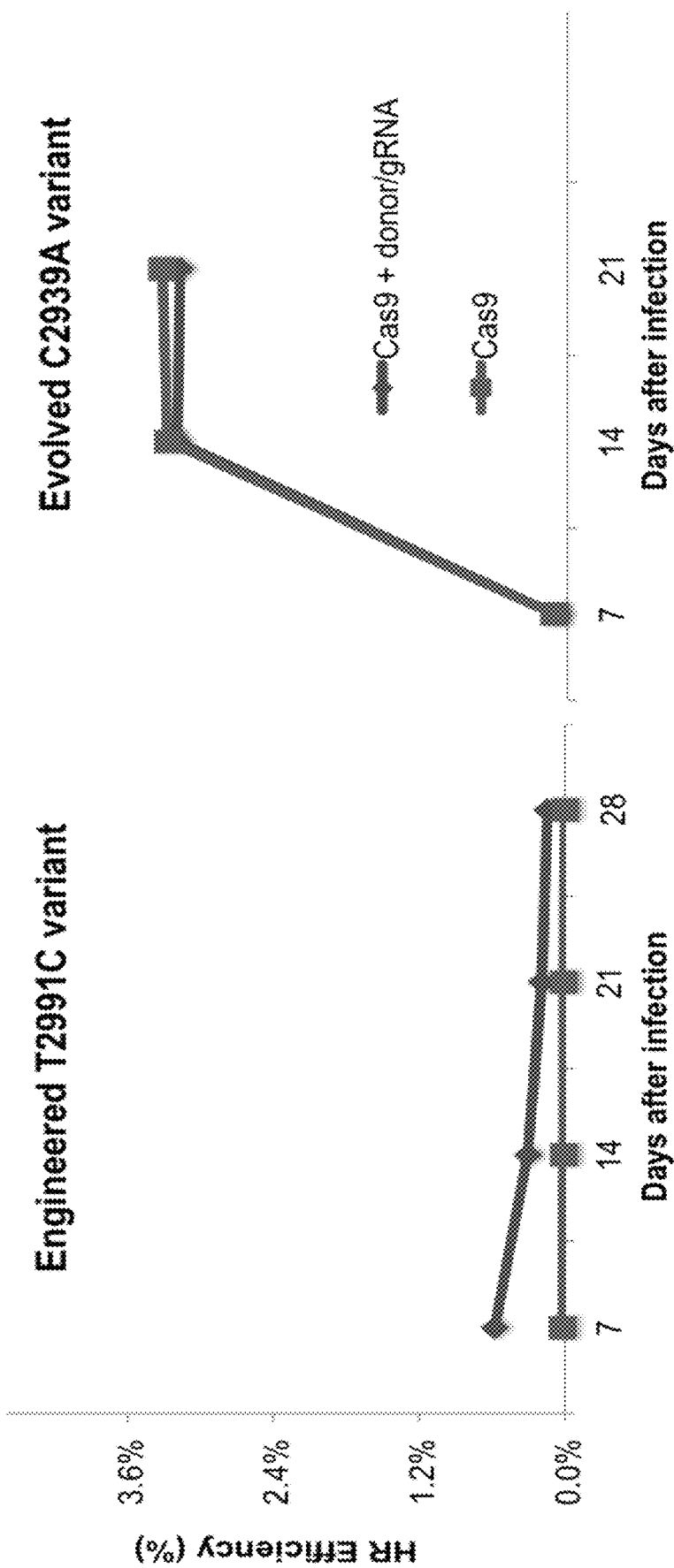
FIG. 6A depicts data directed to homologous recombination efficiency of an engineered T2991C variant.
FIG. 6B depicts data directed to homologous recombination efficiency of an evolved C2923A variant.

Mitochondrial DNA variants C2939A or T2991C are known to confer CAP resistance. See N. Howell, I. Kubacka, Sequence analysis of mitochondrial chloramphenicol resistance mutations in Chinese hamster cells. Mammalian genome: official journal of the International Mammalian *Genome Society* 4, 271-275 (1993) hereby incorporated by reference in its entirety. CAP resistant cell lines were engineered by introducing specific mutations in the mitochondria genome. A mito-AAV-Cas9 and mito-AAV-donor-RNR2$^{T2991C}$-gRNA were constructed and co-transduced to target and modify the RNR2 (16sRNA) gene with a T2991C mutation. See FIG. 2A, 2B, and FIGS. 5A and 5B. HT1080 cells transduced with mito-AAV-Cas9 and HT1080 wild-type served as negative controls. The infected cells were cultured for 7 days under normal conditions to allow the mito-AAVs to dilute out of the cells (Day 0). Next, the infected cells were cultured in 0, 150, 300 and 500 µg/mL CAP and harvested after 7 days. NGS results confirmed introduction of the T2991C variant in HT1080 cells with 0.6% homologous recombination (HR) efficiency (or 25 fold compared to HT1080 cells infected with only mito-AAV-Cas9). See FIG. 2C. Cellular phenotype also confirmed the introduction of the T2991C mutation into the mtDNA, that the engineered cells were 4% viable when exposed to 300 µg/mL CAP compared to 0.79% viability of Cas9-ST and 0.49% viability of wild-type negative controls (ANOVA, p<0.05). See FIG. 2D and FIGS. 6A and 6B. FIGS. 6A and 6B are directed to chloramphenicol selection for engineered mitochondria which suggests a need for an optimized method to enrich for mitochondrial genome engineering in vitro. HT1080 cells were cultured in 250 µg/mL CAP galactose (glucose-free) media over 21 days to enrich for engineered T2991C mutation (green diamond). This environment, while maintaining T2991C enrichment compared to negative (Cas9 only) control (red square) (see FIG. 6A), induced evolved C2939A mutation to confer CAP resistance in all HT1080 cells (see FIG. 6B). As shown in FIG. 6A, engineered T2991C variant drops from 0.6% efficiency to 0.1% compared to a 0.0% baseline in control cell lines over a 28-day period. Alternatively, as shown in FIG. 6B, the background of the C2939A variant increases from 0.1% to 3.3% in both engineered and control cell lines. Accordingly, the methods described herein were used to introduce a specific mitochondrial mutation in a human cell line.

A programmable cell line to model MELAS was created using the methods described herein. To this end, a mito-AAV-Cas9 and a mito-AAV-donor-RNR2$^{T2991C}$-TRNL1$^{A3243G}$-gRNA were co-transduced into PGP1 iPS cells to target and modify both the RNR2 (16sRNA) gene with a T2991C mutation and the TRNL1 (tRNA$^{Leu}$) gene with the A3243G mutation. This system was quantified at 0.3% efficiency HR targeting efficiency of transduced cell lines (14× compared to iPSCs transduced with only mito-AAV-Cas9). See FIG. 2C.

Figure 3A:
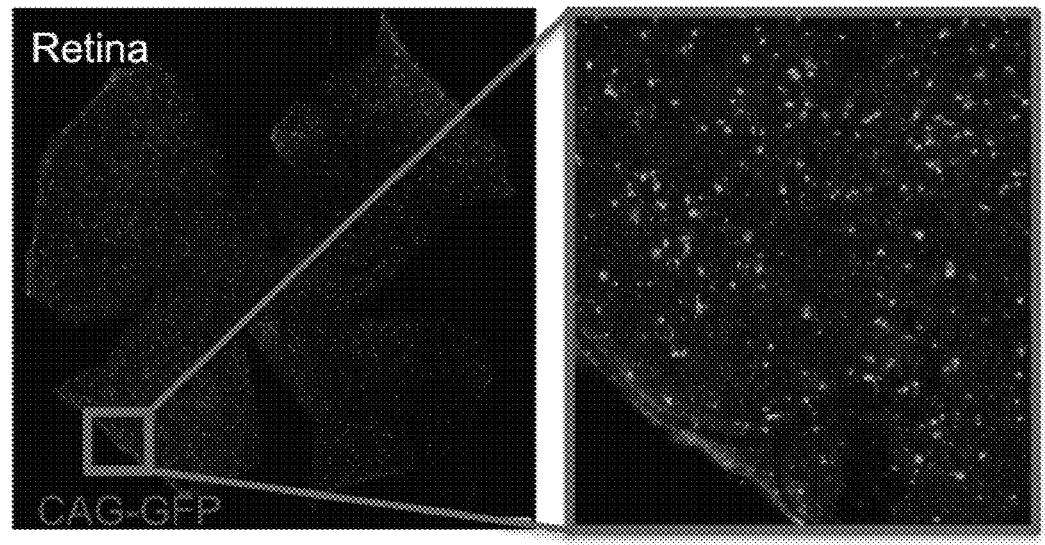
FIG. 3A to FIG. 3B are directed to in vivo mitochondrial genome engineering.
Figure 3B:
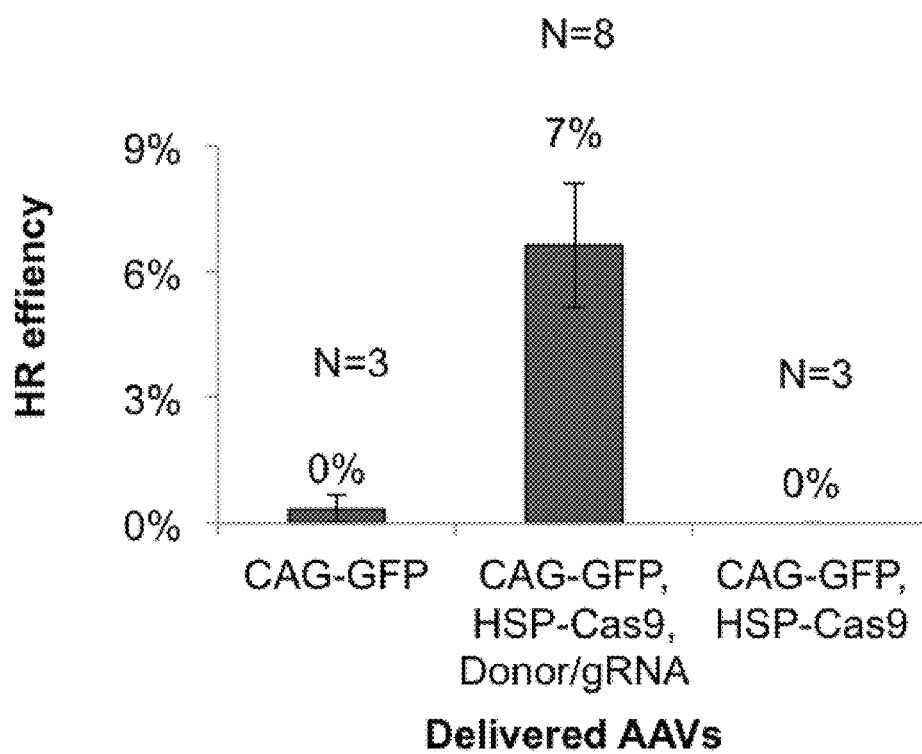

MELAS has been known to affect the retinal ganglion cells. Methods described herein were used to edit the mitochondrial genome of the retina in vivo. Mito-AAV-CRISPR systems were engineered to introduce the A2601G on mtDNA tRNA$^{Leu}$, which aligns to the human A3243G variant. Mito-AAV-Cas9 and mito-AAV-donor-gRNA were co-injected into the mouse eye subretinally, along with mito-AAV-CAG-GFP to track the transduction. Retinas were dissociated and GFP positive cells were enriched and prepared for NGS to quantify the editing efficiency on the targeting site (see FIG. 3A). Notably, the efficiency of editing in vivo mitochondria was about 7% compared to 0% in the negative controls. The in vivo efficiency using infection by AAV is 10 fold higher than the efficiency observed with in vitro models (see FIG. 3B).

Illumina adapter primers used for sequencing are provided below.

| | |
|---|---|
| Gene | TRNL1 |
| Species | Mouse |
| Variant | A2601G |
| Forward primer | ACACTCTTTCCCTACACGACGCTCTTCCGATCGCGC TCTCAACCTAATTTATGA (SEQ ID NO: 1) |
| Reverse primer | GTGACTGGAGTTCAGACGTGTGCTCTTCCGATCTTT GAACCTCTGGGAACAAGG (SEQ ID NO: 2) |
| Gene | TRNL1 |
| Species | Human |
| Variant | A3243G |
| Forward primer | ACACTCTTTCCCTACACGACGCTCTTCCGATCACTT CACAAAGCGCCTTCC (SEQ ID NO: 3) |
| Reverse primer | GTGACTGGAGTTCAGACGTGTGCTCTTCCGATCTGAA GAGGAATTGAACCTCTGACTG (SEQ ID NO: 4) |
| Gene | RNR2 |
| Species | Human |
| Variant | C2939A, T2991C |
| Forward primer | CCCTACACGACGCTCTTCCGATCCAATAACTTGACCA ACGGAACA (SEQ ID NO: 5) |
| Reverse primer | GTTCAGACGTGTGCTCTTCCGATCTACCTTTAATAGC GGCTGCAC (SEQ ID NO: 6) |

Plasmid sequences are provided below as indicated.

Mito-pAAV-GFP
(SEQ ID NO: 7)
CCCACCCCCAATTTTGTATTTATTTATTTTTTAATTATTTTGTGCAGCGA

TGGGGGCGGGGGGGGGGGGGGGCGCGCGCCAGGCGGGGCGGGGCGGGGC

GAGGGGCGGGGCGGGGCGAGGCGGAGAGGTGCGGCGGCAGCCAATCAGAG

CGGCGCGCTCCGAAAGTTTCCTTTTATGGCGAGGCGGCGGCGGCGGCGGC

CCTATAAAAAGCGAAGCGCGCGGCGGGCGGGAGTCGCTGCGACGCTGCCT

TCGCCCCGTGCCCCGCTCCGCCGCCGCCTCGCGCCGCCCGCCCCGGCTCT

-continued

```
GACTGACCGCGTTACTCCCACAGGTGAGCGGGCGGGACGGCCCTTCTCCT
CCCGGGCTGTAATTAGCGCTTGGTTTAATGACGGCTTGTTTCTTTTCTGTG
GCTGCGTGAAAGCCTTGAGGGGCTCCGGGAGGGCCCTTTGTGCGGGGGGA
GCGGCTCGGGGCTGTCCGCGGGGGGACGGCTGCCTTCGGGGGGACGGGG
CAGGGCGGGGTTCGGCTTCTGGCGTGTGACCGGCGGCTCTAGAGCCTCTG
CTAACCATGTTCATGCCTTCTTCTTTTTCCTACAGCTCCTGGGCAACGTG
CTGGTTATTGTGCTGTCTCATCATTTTGGCAAAGAATTGGATCGGGATCC
CCGGGTACCGGTCGCCACCATGGTGAGCAAGGGCGAGGAGCTGTTCACCG
GGGTGGTGCCCATCCTGGTCGAGCTGGACGGCGACGTAAACGGCCACAAG
TTCAGCGTGTCCGGCGAGGGCGAGGGCGATGCCACCTACGGCAAGCTGAC
CCTGAAGTTCATCTGCACCACCGGCAAGCTGCCCGTGCCCTGGCCCACCC
TCGTGACCACCCTGACCTACGGCGTGCAGTGCTTCAGCCGCTACCCCGAC
CACATGAAGCAGCACGACTTCTTCAAGTCCGCCATGCCCGAAGGCTACGT
CCAGGAGCGCACCATCTTCTTCAAGGACGACGGCAACTACAAGACCCGCG
CCGAGGTGAAGTTCGAGGGCGACACCCTGGTGAACCGCATCGAGCTGAAG
GGCATCGACTTCAAGGAGGACGGCAACATCCTGGGGCACAAGCTGGAGTA
CAACTACAACAGCCACAACGTCTATATCATGGCCGACAAGCAGAAGAACG
GCATCAAGGTGAACTTCAAGATCCGCCACAACATCGAGGACGGCAGCGTG
CAGCTCGCCGACCACTACCAGCAGAACACCCCCATCGGCGACGGCCCCGT
GCTGCTGCCCGACAACCACTACCTGAGCACCCAGTCCGCCCTGAGCAAAG
ACCCCAACGAGAAGCGCGATCACATGGTCCTGCTGGAGTTCGTGACCGCC
GCCGGGATCACTCTCGGCATGGACGAGCTGTACAAG
``` pHSP-Cas9-ST1 cassette sequence (SEQ ID NO: 8)
```
CCGCTGCTAACCCCATACCCCGAACCAACCAAACCCCAAAGACACCCCCC
gccaccATGAGCGACCTGGTGCTGGGCCTGGACATCGGCATCGGCAGCGT
GGGCGTGGGCATCCTGAACAAGGTGACCGGCGAGATCATCCACAAGAACA
GTCGCATCTTCCCTGCTGCTCAGGCTGAGAACAACCTGGTGCGCCGCACC
AACCGCCAGGGTCGCCGGCTTGCTCGCCGCAAGAAGCACCGGCGCGTGCG
CCTGAACCGCCTGTTCGAGGAGAGCGGCCTGATCACCGACTTCACCAAGA
TCAGCATCAACCTGAACCCCTACCAGCTGCGCGTGAAGGGCCTGACCGAC
GAGCTGAGCAACGAGGAGCTGTTCATCGCCCTGAAGAACATGGTGAAGCA
CCGCGGCATCAGCTACCTGGACGACGCCAGCGACGACGGCAACAGCAGCG
TGGGCGACTACGCCCAGATCGTGAAGGAGAACAGCAAGCAGCTGGAGACC
AAGACCCCCGGCCAGATCCAGCTGGAGCGCTACCAGACCTACGGCCAGCT
GCGCGGCGACTTCACCGTGGAGAAGGACGGCAAGAAGCACCGCCTGATCA
ACGTGTTCCCCACCAGCGCCTACCGCAGCGAGGCCCTGCGCATCCTGCAG
ACCCAGCAGGAGTTCAACCCCCAGATCACCGACGAGTTCATCAACCGCTA
CCTGGAGATCCTGACCGGCAAGCGCAAGTACTACCACGGCCCCGGCAACG
AGAAGAGCCGCACCGACTACGGCCGCTACCGCACCAGCGGCGAGACCCTG
GACAACATCTTCGGCATCCTGATCGGCAAGTGCACCTTCTACCCCGACGA
GTTCCGCGCCGCCAAGGCCAGCTACACCGCCCAGGAGTTCAACCTGCTGA
ACGACCTGAACAACCTGACCGTGCCCACCGAGACCAAGAAGCTGAGCAAG
GAGCAGAAGAACCAGATCATCAACTACGTGAAGAACGAGAAGGCCATGGG
CCCCGCCAAGCTGTTCAAGTACATCGCCAAGCTGCTGAGCTGCGACGTGG
CCGACATCAAGGGCTACCGCATCGACAAGAGCGGCAAGGCCGAGATCCAC
ACCTTCGAGGCCTACCGCAAGATGAAGACCCTGGAGACCCTGGACATCGA
GCAGATGGACCGCGAGACCCTGGACAAGCTGGCCTACGTGCTGACCCTGA
ACACCGAGCGCGAGGGCATCCAGGAGGCCCTGGAGCACGAGTTCGCCGAC
GGCAGCTTCAGCCAGAAGCAGGTGGACGAGCTGGTGCAGTTCCGCAAGGC
CAACAGCAGCATCTTCGGCAAGGGCTGGCACAACTTCAGCGTGAAGCTGA
TGATGGAGCTGATCCCCGAGCTGTACGAGACCAGCGAGGAGCAGATGACC
ATCCTGACCCGCCTGGGCAAGCAGAAGACCACCAGCAGCAGCAACAAGAC
CAAGTACATCGACGAGAAGCTGCTGACCGAGGAGATCTACAACCCCGTGG
TGGCCAAGAGCGTGCGCCAGGCCATCAAGATCGTGAACGCCGCCATCAAG
GAGTACGGCGACTTCGACAACATCGTGATCGAGATGGCCCGCGAGACCAA
CGAGGACGACGAGAAGAAGGCCATCCAGAAGATCCAGAAGGCCAACAAGG
ACGAGAAGGACGCCGCCATGCTGAAGGCCGCCAACCAGTACAACGGCAAG
GCCGAGCTGCCCCACAGCGTGTTCCACGGCCACAAGCAGCTGGCCACCAA
GATCCGCCTGTGGCACCAGCAGGGCGAGCGCTGCCTGTACACCGGCAAGA
CCATCAGCATCCACGACCTGATCAACAACAGCAACCAGTTCGAGGTGGAC
CACATCCTGCCCCTGAGCATCACCTTCGACGACAGCCTGGCCAACAAGGT
GCTGGTGTACGCCACCGCCAACCAGGAGAAGGGCCAGCGCACCCCCTACC
AGGCCCTGGACAGCATGGACGACGCCTGGAGCTTCCGCGAGCTGAAGGCC
TTCGTGCGCGAGAGCAAGACCCTGAGCAACAAGAAGAAGGAGTACCTGCT
GACCGAGGAGGACATCAGCAAGTTCGACGTGCGCAAGAAGTTCATCGAGC
GCAACCTGGTGGACACCCGCTACGCCAGCCGCGTGGTGCTGAACGCCCTG
CAGGAGCACTTCCGCGCCCACAAGATCGACACCAAGGTGAGCGTGGTGCG
CGGCCAGTTCACCAGCCAGCTGCGCCGCCACTGGGGCATCGAGAAGACCC
GCGACACCTACCACCACCACGCCGTGGACGCCCTGATCATTGCGGCTTCT
AGCCAGCTGAACCTGTGGAAGAAGCAGAAGAACACCCTGGTGAGCTACAG
CGAGGACCAGCTGCTGGACATCGAGACCGGCGAGCTGATCAGCGACGACG
AGTACAAGGAGAGCGTGTTCAAGGCCCCCTACCAGCACTTCGTGGACACC
CTGAAGAGCAAGGAGTTCGAGGACAGCATCCTGTTCAGCTACCAGGTGGA
CAGCAAGTTCAACCGCAAGATCAGCGACGCCACCATCTACGCCACCCGCC
AGGCCAAGGTGGGCAAGGACAAGGCCGACGAGACCTACGTGCTGGGCAAG
ATCAAGGACATCTACACCCAGGACGGCTACGACGCCTTCATGAAGATCTA
CAAGAAGGACAAGAGCAAGTTCCTGATGTACCGCCACGACCCCCAGACCT
TCGAGAAGGTGATCGAGCCCATCCTGGAGAACTACCCCAACAAGCAGATC
AACGATAAAGGCAAGGAGGTGCCCTGCAACCCCTTCCTGAAGTACAAGGA
GGAGCACGGCTACATCCGCAAGTACAGCAAGAAGGGCAACGGCCCCGAGA
TCAAGAGCCTGAAGTACTACGACAGCAAGCTGGGCAACCACATCGACATC
```

-continued

ACCCCCAAGGACAGCAACAACAAGGTGGTGCTGCAGAGCGTGAGCCCCTG
GCGCGCCGACGTGTACTTCAACAAGACCACCGGCAAGTACGAGATCCTGG
GCCTGAAGTACGCCGACCTGCAGTTTGATAAGGGCACCGGCACCTACAAG
ATCAGCCAGGAGAAGTACAACGACATCAAGAAGAAGGAGGGCGTGGACAG
CGACAGCGAGTTCAAGTTCACCCTGTACAAGAACGACCTTCTGCTGGTGA
AGGACACCGAGACCAAGGAGCAACAGCTGTTCCGCTTCCTGAGCCGCACC
ATGCCCAAGCAGAAGCACTACGTGGAGCTGAAGCCCTACGACAAGCAGAA
GTTCGAGGGCGGCGAGGCCCTGATCAAGGTGCTGGGCAACGTGGCCAACA
GCGGCCAGTGCAAGAAGGGCCTGGGCAAGAGCAACATCAGCATCTACAAG
GTGCGCACCGACGTGCTGGGCAACCAGCACATCATCAAGAACGAGGGCGA
CAAGCCCAAGCTGGACTTCtaa Mito-pAAV-Donor RNR2$^{T2991C}$-TRNL1$^{A3243G}$-gRNA
(SEQ ID NO: 9)

AGCGCCCAATACGCAAACCGCCTCTCCCCGCGCGTTGGCCGATTCATTAA
TGCAGCTGCGCGCTCGCTCGCTCACTGAGGCCGCCCGGGCAAAGCCCGGG
CGTCGGGCGACCTTTGGTCGCCCGGCCTCAGTGAGCGAGCGAGCGCGCAG
AGAGGGAGTGGCCAACTCCATCACTAGGGGTTCCTTGTAGTTAATGATTA
ACCCGCCATGCTACTTATCTACGTAGCCATGCTCTAGGAAGATCGTACCA
TTGACGTCAATAATGACGTATGTTCCCATAGTAACGCCAATAGGGACTTT
CCATTGACGTCAATGGGTGGACTATTTACGGTAAACTGCCCACTTGGCAG
TACATCAAGTGTATCATATGCCAAGTACGCCCCCTATTGACGTCAATGAC
GGTAAATGGCCCGCCTGGCATTATGCCCAGTACATGACCTTATGGGACTT
TCCTACTTGGCAGTACATCTACGTATTAGTCATCGCTATTACCATGGTTA
GCTGGTTGTCCAAGATAGAATCTTAGTTCAACTTTAAATTTGCCCACAGA
ACCCTCTAAATCCCCTTGTAAATTTAACTGTTAGTCCAAAGAGGAACAGC
TCTTTGGACACTAGGAAAAAACCTTGTAGAGAGAGTAAAAAATTTAACAC
CCATAGTAGGCCTAAAAGCAGCCACCAATTAAGAAAGCGTTCAAGCTCAA
CACCCACTACCTAAAAAATCCCAAACATATAACTGAACTCCTCACACCCA
ATTGGACCAATCTATCACCCTATAGAAGAACTAATGTTAGTATAAGTAAC
ATGAAAACATTCTCCTCCGCATAAGCCTGCGTCAGATTAAAACACTGAAC
TGACAATTAACAGCCCAATATCTACAATCAACCAACAAGTCATTATTACC
CTCACTGTCAACCCAACACAGGCATGCTCATAAGGAAAGGTTAAAAAAAG
TAAAAGGAACTCGGCAAATCTTACCCCGCCTGTTTACCAAAAACATCACC
TCTAGCATCACCAGTATTAGAGGCACCGCCTGCCCAGTGACACATGTTTA
ACGGCCGCGGTACCCTAACCGTGCAAAGGTAGCATAATCACTTGTTCCTT
AAATAGGGACCTGTATGAATGGCTCCACGAGGGTTCAGCTGTCTCTTACT
TTTAACCAGTGAAATTGACCTGCCCGTGAAGAGGCGGGCATAACACAGCA
AGACGAGAAGACCCTATGGAGCTTTAATTTATTAATGCAAACAGTACCTA
ACAAACCCACAGGTCCTAAACTACCAAACCTGCATTAAAAATTTCGGTTG
GGGCGACCTCGGAGCAGAACCCAACCTCCGAGCAGTACATGCTAAGACTT
CACCAGTCAAAGCGAACTACTATACTCAATTGATCCAATAACTTGACCAA
CGGAACAAGTTACCCTAGGGATAACAGCGCAATCCTATTCTAGAGTCCAT

-continued

ATCAACAATAGGGTTTACGACCTCGACGTTGGATCAGGACATCCCGATGG
TGCAGCCGCTATTAAAGGTTCGTTTGTTCAACGATTAAAGTCCTACGTGA
TCTGAGTTCAGACCGGAGTAATCCAGGTCGGTTTCTATCTACNTTCAAAT
TCCTCCCTGTACGAAAGGACAAGAGAAATAAGGCCTACTTCACAAAGCGC
CTTCCCCCGTAAATGATATCATCTCAACTTAGTATTATACCCACACCCAC
CCAAGAACAGGGTTTGTTAAGATGGCAGGGCCCGGTAATCGCATAAAACT
TAAAACTTTACAGTCAGAGGTTCAATTCCTCTTCTTAACAACATACCCAT
GGCCAACCTCCTACTCCTCATTGTACCCATTCTAATCGCAATGGCATTCC
TAATGCTTACCGAACGAAAAATTCTAGGCTATATACAACTACGCAAAGGC
CCCAACGTTGTAGGCCCCTACGGGCTACTACAACCCTTCGCTGACGCCAT
AAAACTCTTCACCAAAGAGCCCCTAAAACCCGCCACATCTACCATCACCC
TCTACATCACCGCCCCGACCTTAGCTCTCACCATCGCTCTTCTACTATGA
ACCCCCCTCCCCATACCCAACCCCCTGGTCAACCTCAACCTAGGCCTCCT
ATTTATTCTAGCCACCTCTAGCCTAGCCGTTTACTCAATCCTCTGATCAG
GGTGAGCATCAAACTCAAACTACGCCCTGATCGGCGCACTGCGAGCAGTA
GCCCAAACAATCTCATATGAAGTCACCCTAGCCATCATTCTACTATCAAC
ATTACTAATAAGTGGCTCCTTTAACCTCTCCACCCTTATCACAACACAAG
AACACCTCTGATTACTCCTGCCATCATGACCCTTGGCCATAATATGATTT
ATCTCCACACTAGCAGAGACCAACCGAACCCCCTTCGACCTTGCCGAAGG
GGAGTCCGAACTAGTCTCAGGCTTCAACATCGAATACGCCGCAGGCCCCT
TCGCCCTATTCTTCATAGCCGAATACACAAACATTATTATAATAAACACC
CTCACCACTACAATCTTCCTAGGAACAACAATTAGCGCTTGGTTTAATGA
CGGCTTGTTTCTTTT<u>CTGTACAAAAAAGCAGGCTTTAAAGGAACCAATTC</u>
<u>AGTCGACTGGATCCGGTACCAAGGTCGGGCAGGAAGAGGGCCTATTTCCC</u>
<u>ATGATTCCTTCATATTTGCATATACGATACAAGGCTGTTAGAGAGATAAT</u>
<u>TAGAATTAATTTGACTGTAAACACAAAGATATTAGTACAAAATACGTGAC</u>
<u>GTAGAAAGTAATAATTTCTTGGGTAGTTTGCAGTTTTAAAATTATGTTTT</u>
<u>AAAATGGACTATCATATGCTTACCGTAACTTGAAAGTATTTCGATTTCTT</u>
<u>GGCTTTATATATCTTGTGGAAAGGACGAAACACCGGATAACAGCGCAATC</u>
<u>CTATTGTTTTTGTACTCTCAGAAATGCAGAAGCTACAAAGATAAGGCTTC</u>
<u>ATGCCGAAATCAACACCCTGTCATTTTATGGCAGGGTGTTTTTTTGACCT</u>
<u>TGCCGAAGGGGAGTCCGAACTAGTCTCAGATGTACAAAAAAGCAGGCTTT</u>
<u>AAAGGAACCAATTCAGTCGACTGGATCCGGTACCAAGGTCGGGCAGGAAG</u>
<u>AGGGCCTATTTCCCATGATTCCTTCATATTTGCATATACGATACAAGGCT</u>
<u>GTTAGAGAGATAATTAGAATTAATTTGACTGTAAACACAAAGATATTAGT</u>
<u>ACAAAATACGTGACGTAGAAAGTAATAATTTCTTGGGTAGTTTGCAGTTT</u>
<u>TAAAATTATGTTTTAAAATGGACTATCATATGCTTACCGTAACTTGAAAG</u>
<u>TATTTCGATTTCTTGGCTTTATATATCTTGTGGAAAGGACGAAACACCGT</u>
<u>TTACGACCTCGATGTTGGAGTTTTTGTACTCTCAGAAATGCAGAAGCTAC</u>
<u>AAAGATAAGGCTTCATGCCGAAATCAACACCCTGTCATTTTATGGCAGGG</u>

TGTTTTTTTAAGTTAACAACAACAATTGCATTCATTTTATGTTTCAGGTT
CAGGGGGAGATGTGGGAGGTTTTTTAAAGCAAGTAAAACCTCTACAAATG
TGGTAAAATCGATAAGGATCTTCCTAGAGCATGGCTACGTAGATAAGTAG
CATGGCGGGTTAATCATTAACTACAAGGAACCCCTAGTGATGGAGTTGGC
CACTCCCTCTCTGCGCGCTCGCTCGCTCACTGAGGCCGGGCGACCAAAGG
TCGCCCGACGCCCGGGCTTTGCCCGGGCGGCCTCAGTGAGCGAGCGAGCG
CGCAGCCTTAATTAACCTAATTCACTGGCCGTCGTTTTACAACGTCGTGA
CTGGGAAAACCCTGGCGTTACCCAACTTAATCGCCTTGCAGCACATCCCC
CTTTCGCCAGCTGGCGTAATAGCGAAGAGGCCCGCACCGATCGCCCTTCC
CAACAGTTGCGCAGCCTGAATGGCGAATGGGACGCGCCCTGTAGCGGCGC
ATTAAGCGCGGCGGGTGTGGTGGTTACGCGCAGCGTGACCGCTACACTTG
CCAGCGCCCTAGCGCCCGCTCCTTTCGCTTTCTTCCCTTCCTTTCTCGCC
ACGTTCGCCGGCTTTCCCCGTCAAGCTCTAAATCGGGGGCTCCCTTTAGG
GTTCCGATTTAGTGCTTTACGGCACCTCGACCCCAAAAAACTTGATTAGG
GTGATGGTTCACGTAGTGGGCCATCGCCCTGATAGACGGTTTTTCGCCCT
TTGACGTTGGAGTCCACGTTCTTTAATAGTGGACTCTTGTTCCAAACTGG
AACAACACTCAACCCTATCTCGGTCTATTCTTTTGATTTATAAGGGATTT
TGCCGATTTCGGCCTATTGGTTAAAAAATGAGCTGATTTAACAAAAATTT
AACGCGAATTTTAACAAATATTAACGCTTACAATTTAGGTGGCACTTTT
CGGGGAAATGTGCGCGGAACCCCTATTTGTTTATTTTTCTAAATACATTC
AAATATGTATCCGCTCATGAGACAATAACCCTGATAAATGCTTCAATAAT
ATTGAAAAGGAAGAGTATGAGTATTCAACATTTCCGTGTCGCCCTTATT
CCCTTTTTTGCGGCATTTTGCCTTCCTGTTTTTGCTCACCCAGAAACGCT
GGTGAAAGTAAAAGATGCTGAAGATCAGTTGGGTGCACGAGTGGGTTACA
TCGAACTGGATCTCAACAGCGGTAAGATCCTTGAGAGTTTTCGCCCCGAA
GAACGTTTTCCAATGATGAGCACTTTTAAAGTTCTGCTATGTGGCGCGGT
ATTATCCCGTATTGACGCCGGGCAAGAGCAACTCGGTCGCCGCATACACT
ATTCTCAGAATGACTTGGTTGAGTACTCACCAGTCACAGAAAAGCATCTT
ACGGATGGCATGACAGTAAGAGAATTATGCAGTGCTGCCATAACCATGAG

TGATAACACTGCGGCCAACTTACTTCTGACAACGATCGGAGGACCGAAGG
AGCTAACCGCTTTTTTGCACAACATGGGGGATCATGTAACTCGCCTTGAT
CGTTGGGAACCGGAGCTGAATGAAGCCATACCAAACGACGAGCGTGACAC
CACGATGCCTGTAGCAATGGCAACAACGTTGCGCAAACTATTAACTGGCG
AACTACTTACTCTAGCTTCCCGGCAACAATTAATAGACTGGATGGAGGCG
GATAAAGTTGCAGGACCACTTCTGCGCTCGGCCCTTCCGGCTGGCTGGTT
TATTGCTGATAAATCTGGAGCCGGTGAGCGTGGGTCTCGCGGTATCATTG
CAGCACTGGGGCCAGATGGTAAGCCCTCCCGTATCGTAGTTATCTACACG
ACGGGGAGTCAGGCAACTATGGATGAACGAAATAGACAGATCGCTGAGAT
AGGTGCCTCACTGATTAAGCATTGGTAACTGTCAGACCAAGTTTACTCAT
ATATACTTTAGATTGATTTAAAACTTCATTTTTAATTTAAAAGGATCTAG
GTGAAGATCCTTTTTGATAATCTCATGACCAAAATCCCTTAACGTGAGTT
TTCGTTCCACTGAGCGTCAGACCCCGTAGAAAAGATCAAAGGATCTTCTT
GAGATCCTTTTTTTCTGCGCGTAATCTGCTGCTTGCAAACAAAAAAACCA
CCGCTACCAGCGGTGGTTTGTTTGCCGGATCAAGAGCTACCAACTCTTTT
TCCGAAGGTAACTGGCTTCAGCAGAGCGCAGATACCAAATACTGTTCTTC
TAGTGTAGCCGTAGTTAGGCCACCACTTCAAGAACTCTGTAGCACCGCCT
ACATACCTCGCTCTGCTAATCCTGTTACCAGTGGCTGCTGCCAGTGGCGA
TAAGTCGTGTCTTACCGGGTTGGACTCAAGACGATAGTTACCGGATAAGG
CGCAGCGGTCGGGCTGAACGGGGGGTTCGTGCACACAGCCCAGCTTGGAG
CGAACGACCTACACCGAACTGAGATACCTACAGCGTGAGCTATGAGAAAG
CGCCACGCTTCCCGAAGGGAGAAAGGCGGACAGGTATCCGGTAAGCGGCA
GGGTCGGAACAGGAGAGCGCACGAGGGAGCTTCCAGGGGGAAACGCCTGG
TATCTTTATAGTCCTGTCGGGTTTCGCCACCTCTGACTTGAGCGTCGATT
TTTGTGATGCTCGTCAGGGGGCGGAGCCTATGGAAAAACGCCAGCAACG
CGGCCTTTTTACGGTTCCTGGCCTTTTGCTGGCCTTTTGCTCACATGTTC
TTTCCTGCGTTATCCCCTGATTCTGTGGATAACCGTATTACCGCCTTTGA
GTGAGCTGATACCGCTCGCCGCAGCCGAACGACCGAGCGCAGCGAGTCAG
TGAGCGAGGAAGCGGAAG

What is claimed is:

1. A method of altering mitochondrial DNA of a eukaryotic cell comprising
providing to the eukaryotic cell a first mito-specific adeno-associated virus vector including a first nucleic acid sequence encoding a guide RNA sequence complementary to a target mitochondrial nucleic acid sequence and a mitochondrial specific promoter and mitochondrial specific start and stop codons,
providing to the eukaryotic cell a second mito-specific adeno-associated virus vector including a second nucleic acid sequence encoding a Cas9 enzyme that interacts with the guide RNA sequence and cleaves the target mitochondrial nucleic acid sequence in a site specific manner and a mitochondrial specific promoter and mitochondrial specific start and stop codons,
wherein the first vector delivers the first nucleic acid sequence into the mitochondria of the eukaryotic cell, wherein the first nucleic acid sequence is expressed,
wherein the second vector delivers the second nucleic acid sequence into the mitochondria of the eukaryotic cell, wherein the second nucleic acid sequence is expressed,
wherein the guide RNA sequence binds to the complementary target mitochondrial nucleic acid sequence and the Cas9 enzyme cleaves the target mitochondrial nucleic acid sequence in a site specific manner.

2. The method of claim 1 further including the step of providing a donor sequence into the mitochondria and wherein the donor sequence is inserted into the mitochondrial DNA.

3. The method of claim 2 wherein the donor nucleic acid sequence and the gRNA are connected.

4. The method of claim 1 wherein the first vector includes a third nucleic acid sequence encoding a donor nucleic acid sequence.

5. The method of claim 1 wherein the eukaryotic cell is a yeast cell, a plant cell or a mammalian cell.

6. The method or claim 1 wherein the eukaryotic cell is a human cell.

7. The method of claim 1 wherein a plurality of guide RNAs are provided into the mitochondria that are complementary to different target mitochondrial nucleic acid sequences and the Cas9 enzyme cleaves the different target mitochondrial nucleic acid sequences in a site specific manner.

* * * * *